United States Patent
Stepany et al.

(10) Patent No.: US 11,168,339 B1
(45) Date of Patent: Nov. 9, 2021

(54) PROCESSES AND SYSTEMS FOR ANAEROBIC DIGESTION OF LIGNOCELLULOSIC BIOMASS AND ORGANIC WASTES

(71) Applicant: CBG Partners, LLC, San Anselmo, CA (US)

(72) Inventors: Peter Stepany, Schwarzach (AT); John McKinney, San Rafael, CA (US); Roland Kirchmayr, Maeder (AT)

(73) Assignee: CBG Partners, LLC, San Anselmo, CA (US)

( * ) Notice: Subject to any disclaimer, the term of this patent is extended or adjusted under 35 U.S.C. 154(b) by 83 days.

(21) Appl. No.: 16/211,618

(22) Filed: Dec. 6, 2018

Related U.S. Application Data

(60) Provisional application No. 62/598,693, filed on Dec. 14, 2017.

(51) Int. Cl.
  *C12P 5/02* (2006.01)

(52) U.S. Cl.
  CPC ........... *C12P 5/023* (2013.01); *C12P 2201/00* (2013.01); *C12P 2203/00* (2013.01)

(58) Field of Classification Search
  CPC ......... C02F 11/04; C12M 21/04; C12P 5/023; C12P 2203/00; C12P 2201/00
  See application file for complete search history.

(56) References Cited

U.S. PATENT DOCUMENTS

| | | | | |
|---|---|---|---|---|
| 7,033,822 | B2* | 4/2006 | Maston | C12M 21/04 210/180 |
| 8,247,009 | B2* | 8/2012 | Datta | B01D 53/84 426/56 |
| 8,758,615 | B2* | 6/2014 | Smith | C12M 41/48 210/603 |
| 9,145,315 | B2* | 9/2015 | Stephenson | C02F 3/1221 |
| 2008/0124775 | A1* | 5/2008 | Kovacs | C02F 3/34 435/167 |
| 2013/0323714 | A1* | 12/2013 | Cheng | C12M 41/34 435/3 |
| 2016/0200002 | A1* | 7/2016 | Medoff | C12P 19/02 264/470 |
| 2016/0289720 | A1* | 10/2016 | Redford | C12M 39/00 |
| 2018/0002206 | A1* | 1/2018 | Assadi | C02F 9/00 |
| 2019/0284075 | A1* | 9/2019 | Zhang | C02F 11/12 |

FOREIGN PATENT DOCUMENTS

| | | | | |
|---|---|---|---|---|
| WO | WO-2013022998 | A2 * | 2/2013 | C07C 51/16 |

OTHER PUBLICATIONS

Stelte et al., Biomass Pelletization Review, 2012, BioResources 7(3), pp. 4451-4490 (Year: 2012).*
Zheng et al., Extrusion Pretreatment of Lignocellulosic Biomass: A Review, International Journal of Molecular Sciences, vol. 15(2014), pp. 18967-18984 (Year: 2014).*
Cavani et al., Chemicals and Fuels from Bio-Based Building Blocks, vol. 1 (2016), pp. 500-502 (Year: 2016).*

* cited by examiner

*Primary Examiner* — Lynn Y Fan
(74) *Attorney, Agent, or Firm* — Hamre, Schumann, Mueller & Larson, P.C.

(57) ABSTRACT

Process and systems are provided for anaerobic digestion of lignocellulosic feedstock into biogas and co-products, such as fibrous humid cake and a fine-particles slurry. The feedstock (e.g., grass straw) is typically first ground or milled. The feedstock is subjected to pelletizing or extruding to generate pellets (e.g., cubes) or extrudates. The pellets or extrudates may be fed to a hydrolysis unit or a digester, in dry form or wet form. Various chemicals may be added to improve the mechanical disintegration of the lignocellulosic structure of the feedstock, before, during, or after formation of pellets or extrudates. The biogas may be stored, sold, used, or further treated, such as via purification to produce pipeline-quality cellulosic methane. The fibrous humid cake and the fine-solids slurry have many potential uses. Other potential co-products include lignin, biochar, energy (as heat and/or electricity), fertilizers, soil or land conditioners, ammonium sulfate, ammonium hydroxide, and carbon dioxide.

43 Claims, 20 Drawing Sheets

PROCESSES AND SYSTEMS FOR ANAEROBIC DIGESTION OF LIGNOCELLULOSIC BIOMASS AND ORGANIC WASTES

PRIORITY DATA

This patent application is a non-provisional patent application with priority to U.S. Provisional Patent App. No. 62/598,693, filed on Dec. 14, 2017, which is hereby incorporated by reference herein.

FIELD

The present invention generally relates to anaerobic digestion of various feedstocks, such as lignocellulosic biomass and organic waste materials.

BACKGROUND

Anaerobic digestion is a series of biological processes in which microorganisms break down biodegradable material in the absence of oxygen. One of the end products is biogas, which may be combusted to generate electricity and heat, or processed into renewable natural gas, transportation fuels, or chemicals. Known anaerobic digestion technologies can convert livestock manure, municipal wastewater solids, food waste, industrial wastewater residuals, fats, oils, grease, and various other organic waste streams into biogas. Separated digested solids can be composted, utilized for dairy bedding, directly applied to cropland, or converted into other products. Nutrients in the liquid stream may be used in agriculture as fertilizer.

"Biogas" refers to a mixture of different gases produced by the breakdown of organic matter in the absence of oxygen. Biogas is a renewable energy source. The composition of biogas varies depending upon the substrate composition, as well as the conditions within the anaerobic reactor (such as temperature, pH, and substrate concentration). In addition to methane, biogas typically also contains carbon dioxide, carbon monoxide, hydrogen, water, nitrogen, and sulfur. The methane provides energy value to the biogas.

Starting in 2002, the construction of biogas plants significantly increased when Austria and Germany introduced guaranteed feed-in tariffs and passed favorable renewable energy legislation. The result was the construction of more than 9,000 biogas plants in Germany alone. The first biogas plants built were initially of simple design and subsequent plant designs evolved based on experience gained in engineering and operating the early plants.

The conventional digestion process begins with bacterial hydrolysis of the input materials in order to break down insoluble organic polymers such as carbohydrates and make them available for other bacteria. Acidogenic bacteria then convert the sugars and amino acids into carbon dioxide, hydrogen, ammonia, and organic acids. Acetogenic bacteria convert the organic acids into acetic acid, along with additional ammonia, hydrogen, and carbon dioxide. Finally, methanogens convert these products to methane and carbon dioxide.

Improvements to anaerobic digestion are still desired in order to economically convert a range of feedstocks, and to generate high-value co-products in addition to biogas, in a biorefinery process and system.

Feeding lignocellulosic biomass such as straw or corn stover into process tanks containing liquids, and mixing the biomass into the liquid content of such tanks, is known to be challenging. The problem is known for example from the cellulosic ethanol industry, which is facing serious challenges for feeding dry lignocellulosic biomass into process tanks such as hydrolysis, liquefaction, or fermentation tanks. Achieving a good distribution of the dry lignocellulosic feedstock into the liquid of such process tanks is desired, to allow for a good biochemical or chemical interaction and reaction of the process tank liquid with the biomass. Good distribution of lignocellulosic feedstock into liquid will improve hydrolysis, bacteriological access of microorganisms to the lignocellulosic biomass, and/or good interaction of added chemicals or added enzymes with the lignocellulosic biomass to support the desired effect of chemicals or enzymes. The desired effects on the biomass may include opening or weakening the lignocellulosic structure of the feedstock, or enhancing the release of sugar oligomers from the lignocellulosic biomass, for example.

Improvements to biomass feeding methods and systems are therefore desired in order to economically process a range of lignocellulosic feedstocks, for producing biogas or other products.

SUMMARY OF EMBODIMENTS

Some variations provide a process for converting a lignocellulosic feedstock into methane, the process comprising:

(a) grinding or milling a lignocellulosic feedstock, to generate a size-reduced lignocellulosic material;

(b) introducing a pretreatment chemical to the size-reduced lignocellulosic material;

(c) pelletizing or extruding the size-reduced lignocellulosic material, to generate a plurality of lignocellulosic pellets or extrudates;

(d) feeding the lignocellulosic pellets or extrudates, or a slurry formed therefrom, into one or more anaerobic digesters operated at effective fermentation conditions to generate methane-containing biogas and a digester slurry; and (e) recovering the methane-containing biogas from the one or more anaerobic digesters.

The lignocellulosic feedstock may be selected from the group consisting of grass straw, wheat straw, corn stover, grain straw, rice straw, cotton burr, sugarcane bagasse, and combinations thereof, for example. The size-reduced lignocellulosic material may have an average maximum particle size of about 1 inch or less.

In some embodiments, a waste feedstock is also fed to one or more anaerobic digesters. The waste feedstock may be selected from the group consisting of food waste, agricultural organic waste, industrial organic waste, livestock manure, and combinations thereof. The weight ratio of the lignocellulosic feedstock to the waste feedstock (when present) is preferably selected from about 0.3 to about 3.0.

The pretreatment chemical may be selected from the group consisting of sodium hydroxide, potassium hydroxide, calcium carbonate, ammonia, acetic acid, phosphoric acid, urea, carbon dioxide, salts of any of the foregoing, and combinations thereof. The pretreatment chemical may be present in a concentration from about 0.1 wt % to about 10 wt % based on the combined weight of the size-reduced lignocellulosic material and the pretreatment chemical, on a dry basis.

In some embodiments, steps (b) and (c) are sequential, but the order may be reversed. In certain embodiments, steps (b) and (c) are performed simultaneously.

The lignocellulosic pellets or extrudates may be in the form of lignocellulosic cubes (which in this disclosure includes cuboids). The lignocellulosic cubes may have an average minimum length scale selected from about 0.1 inch to about 6 inches, such as from about 0.5 inch to about 2 inches, and/or an average maximum length scale selected from about 0.5 inch to about 12 inches.

The lignocellulosic pellets or extrudates may be in the form of lignocellulosic briquettes.

Step (c) may include pelletizing at a pelletizing temperature selected from about 25° C. to about 150° C., such as from about 50° C. to about 100° C.

In some embodiments, step (c) includes extruding to generate lignocellulosic extrudates (extruded material from an extruder). The extruding may be carried out at an extrusion temperature selected from about 50° C. to about 250° C., such as from about 100° C. to about 200° C., for example. The lignocellulosic extrudates may be formed in a double-screw extruder, such as one configured with two counter-rotating screws. The counter-rotating screws, in some embodiments, each have an average screw diameter of at least 4 inches and/or each have a ratio of screw length to screw diameter less than 5.

The lignocellulosic pellets or extrudates may be conveyed from a first location to a second location within the process. It is possible to feed the lignocellulosic pellets or extrudates directly into an anaerobic digester or another unit, or to first generate a slurry from the lignocellulosic pellets or extrudates, and then feeding that slurry to the anaerobic digester or other unit.

Step (d) may include forming a slurry from at least some of the lignocellulosic pellets or extrudates, and then feeding the slurry into one or more anaerobic digesters. The slurry may be formed in a mixing tank or hydrolysis unit disposed upstream of the one or more anaerobic digesters.

In some embodiments, the process comprises a hydrolysis step including (i) hydrolysis of the size-reduced lignocellulosic material and/or (ii) hydrolysis of a slurry formed from the lignocellulosic pellets or extrudates, prior to step (d).

The hydrolysis step preferably includes enzymatic hydrolysis. In some embodiments, the hydrolysis step is assisted with micro-aeration of the size-reduced lignocellulosic material and/or the slurry formed from the lignocellulosic pellets or extrudates. The hydrolysis step may be conducted at a hydrolysis temperature selected from about 50° C. to about 70° C., for example. When a hydrolysis step is part of the process, optionally the process further includes recycling digester slurry, or a solid digestate derived therefrom, back to the hydrolysis step.

The effective fermentation conditions may include a fermentation temperature selected from about 20° C. to about 70° C., such as from about 50° C. to about 60° C.

The effective fermentation conditions may include a fermentation pH selected from about 6.5 to about 8.5, such as from about 7.0 to about 8.0.

The effective fermentation conditions may include a fermentation time selected from about 5 days to about 60 days.

The effective fermentation conditions may include the presence of a thermophilic microorganism, mesophilic microorganism, or both of these. Multiple types of microorganisms may be present in a given digester.

The effective fermentation conditions may include the presence of enzymes to enhance degradation rate of cellulose and/or hemicellulose. In some embodiments, the process further comprises a post-digestion step wherein enzymes are added to enhance degradation rate of residual lignocellulosic fibers.

The effective fermentation conditions may include a total suspended solids from about 1 wt % to about 40 wt %, such as from about 5 wt % to about 20 wt %. The organic dry matter content may be from about 30 wt % to about 90 wt % of the total suspended solids, for example.

The methane-containing biogas may be purified to generate an upgraded biogas with higher methane content compared to the methane-containing biogas. In some embodiments, the upgraded biogas contains at least 90 vol % methane, such as at least 97 vol % methane.

The methane-containing biogas, or an upgraded form thereof, may be stored, sold, used, or further treated to provide a gaseous fuel, a liquid fuel, renewable compressed or liquefied natural gas, cellulosic methane, dimethyl ether, syngas, hydrogen, or a combination thereof.

The methane-containing biogas typically contains carbon dioxide, which may be separated and recovered for recycling in the process or for other uses. In some embodiments, at least some of the carbon dioxide is sequestered into a geological formation, such as an oil well for enhanced oil recovery.

In some embodiments, the process further comprises recovery of a nitrogen-containing compound directly from the digester slurry, without first separating the slurry into a solid phase and a liquid phase.

The process typically (but not necessarily) includes separating the digester slurry into a liquid digestate and a solid digestate.

The liquid digestate may be recovered as a co-product, such as a nitrogen-containing compound. The liquid digestate may be recovered as a co-product selected from the group consisting of a fuel, biochar, pyrolysis oil, soil conditioner, agricultural fertilizer, organic soil product, soil enhancement material, landfill conditioner, and combinations thereof. In certain embodiments, the co-product is a fine-particles slurry containing from about 1 wt % to about 10 wt % total solids, from about 0.2 wt % to about 4 wt % nitrogen (elemental N basis), from about 0.05 wt % to about 2 wt % phosphorous (element P basis), and from about 0.1 wt % to about 2 wt % potassium (element K basis).

The liquid digestate may be recycled within the process. For example, the liquid digestate (or a portion thereof) may be recycled to step (b) and/or step (c). In some embodiments, recycled liquid digestate is utilized to directly generate steam that steam-extracts or steam-explodes the size-reduced lignocellulosic material and/or the lignocellulosic pellets or extrudates. In some embodiments, liquid digestate is recycled to step (d), wherein the liquid digestate has a ratio of carbon to nitrogen, on an elemental weight basis, of 30 or less. Liquid digestate may also be combusted to provide digestate energy, wherein the digestate energy is utilized elsewhere within the process.

The solid digestate may be recovered as a co-product, such as a co-product selected from the group consisting of a solid fuel, biochar, pyrolysis oil, soil conditioner, agricultural fertilizer, organic soil product, soil enhancement material, landfill conditioner, and combinations thereof. In certain embodiments, the solid digestate co-product is a fibrous humid cake containing from about 10 wt % to about 50 wt % total solids, from about 0.1 wt % to about 2 wt % nitrogen (elemental N basis), from about 0.1 wt % to about 3 wt % phosphorous (element P basis), and from about 0.05 wt % to about 1 wt % potassium (element K basis).

The solid digestate may be recycled within the process. For example, the solid digestate (or a portion thereof) may be recycled back to one or more anaerobic digesters. Solid digestate may be combusted to provide digestate energy, wherein the digestate energy is utilized elsewhere within the process.

In certain embodiments, solid digestate is gasified to generate syngas. The syngas, or hydrogen contained therein, may be introduced to one or more anaerobic digesters. Alternatively, or additionally, the syngas, or hydrogen contained therein, may be introduced to one or more hydrolysis units within the process. Alternatively, or additionally, the syngas, or hydrogen contained therein, may be introduced to one or more post-digesters within the process.

In certain embodiments, solid digestate is pyrolyzed to generate a pyrolysis solid phase, a pyrolysis liquid phase, and a pyrolysis gas phase. The process may further include feeding a portion of the pyrolysis solid phase to one or more anaerobic digesters and/or to a post-digester disposed downstream of the anaerobic digester(s). The pyrolysis solid phase may act as an activated carbon to adsorb impurities, thereby enhancing biogas yield, for example.

In some embodiments, the process further includes recovery of lignin from the digester slurry. In these or other embodiments, the process further includes recovery of lignin from the liquid digestate and/or from the solid digestate.

Other variations provide a process for converting a lignocellulosic feedstock into methane, the process comprising:

(a) grinding or milling a lignocellulosic feedstock, to generate a size-reduced lignocellulosic material;

(b) pelletizing the size-reduced lignocellulosic material, to generate a plurality of lignocellulosic pellets;

(c) feeding the lignocellulosic pellets, or a slurry formed therefrom, into one or more anaerobic digesters operated at effective fermentation conditions to generate methane-containing biogas and a digester slurry; and (d) recovering the methane-containing biogas from the one or more anaerobic digesters.

In some embodiments, the lignocellulosic pellets are in the form of lignocellulosic cubes, which may have an average minimum length scale selected from about 0.5 inch to about 2 inches, and/or an average maximum length scale selected from about 0.5 inch to about 12 inches.

Step (b) may include pelletizing at a pelletizing temperature selected from about 50° C. to about 100° C.

The lignocellulosic pellets may be conveniently conveyed from a first location to a second location within the process.

In some embodiments, step (c) comprises forming a slurry from at least some of the lignocellulosic pellets, and then feeding the slurry into one or more anaerobic digesters. The slurry may be formed in a mixing tank or hydrolysis unit disposed upstream of one or more anaerobic digesters.

The process may comprise a hydrolysis step including (i) hydrolysis of the size-reduced lignocellulosic material and/or (ii) hydrolysis of a slurry formed from the lignocellulosic pellets, prior to step (c).

The effective fermentation conditions may include a fermentation temperature selected from about 50° C. to about 60° C., a fermentation pH selected from about 7.0 to about 8.0, and a fermentation time selected from about 5 days to about 60 days, for example. The effective fermentation conditions may include presence of a thermophilic microorganism, a mesophilic microorganism, or both a thermophilic microorganism and a mesophilic microorganism.

The methane-containing biogas may be purified to generate an upgraded biogas with at least 90 vol % methane. When the methane-containing biogas contains carbon dioxide (as is typical), the carbon dioxide may be separated and recovered.

In some embodiments, the process further comprises separating the digester slurry into a liquid digestate and a solid digestate.

The liquid digestate may be recovered as a co-product, such as a co-product selected from the group consisting of a fuel, biochar, pyrolysis oil, soil conditioner, agricultural fertilizer, organic soil product, soil enhancement material, landfill conditioner, and combinations thereof. The liquid digestate may be recovered as a fine-particles slurry containing from about 1 wt % to about 10 wt % total solids, from about 0.2 wt % to about 4 wt % nitrogen (elemental N basis), from about 0.05 wt % to about 2 wt % phosphorous (element P basis), and from about 0.1 wt % to about 2 wt % potassium (element K basis).

The solid digestate may be recovered as a co-product, such as a co-product selected from the group consisting of a solid fuel, biochar, pyrolysis oil, soil conditioner, agricultural fertilizer, organic soil product, soil enhancement material, landfill conditioner, and combinations thereof. In certain embodiments, the co-product is a fibrous humid cake containing from about 10 wt % to about 50 wt % total solids, from about 0.1 wt % to about 2 wt % nitrogen (elemental N basis), from about 0.1 wt % to about 3 wt % phosphorous (element P basis), and from about 0.05 wt % to about 1 wt % potassium (element K basis).

Other variations provide a process for converting a lignocellulosic feedstock into methane, the process comprising:

(a) grinding or milling a lignocellulosic feedstock, to generate a size-reduced lignocellulosic material;

(b) introducing a pretreatment chemical to the size-reduced lignocellulosic material;

(c) steam-exploding the size-reduced lignocellulosic material, to generate pretreated lignocellulosic material;

(d) feeding the pretreated lignocellulosic material into one or more anaerobic digesters operated at effective fermentation conditions to generate methane-containing biogas and a digester slurry, wherein the effective fermentation conditions include a temperature from about 50° C. to about 60° C., a pH from about 7 to about 8, a residence time from about 10 days to about 60 days, total suspended solids from about 1 wt % to about 40 wt %, and organic dry matter content from about 30 wt % to about 90 wt % of total suspended solids; and (e) recovering the methane-containing biogas from the one or more anaerobic digesters.

In this process, step (b) may be conducted prior to step (c). Alternatively, step (c) may be conducted prior to step (b). In certain embodiments, step (b) and step (c) are conducted simultaneously.

The pretreatment chemical may be selected from the group consisting of sodium hydroxide, potassium hydroxide, calcium carbonate, ammonia, acetic acid, phosphoric acid, urea, carbon dioxide, salts of any of the foregoing, and combinations thereof. The pretreatment chemical may be present in a concentration from about 0.1 wt % to about 10 wt % based on the combined weight of the size-reduced lignocellulosic material and the pretreatment chemical, on a dry basis.

The process of these variations optionally includes forming lignocellulosic pellets or extrudates from the pretreated lignocellulosic material, prior to step (d). When this is done, step (d) may include forming a slurry from at least some of the lignocellulosic pellets or extrudates, and then feeding the slurry into the one or more anaerobic digesters. Such a slurry may be formed in a mixing tank or hydrolysis unit disposed upstream of the one or more anaerobic digesters, for example.

Still other variations provide a process for converting a lignocellulosic feedstock into methane, the process comprising:

(a) grinding or milling a lignocellulosic feedstock, to generate a size-reduced lignocellulosic material comprising cellulose and lignin;

(b) introducing a solvent for biomass to the size-reduced lignocellulosic material, thereby generating dissolved and/or suspended lignocellulosic material;

(c) introducing a cellulose precipitant to the dissolved and/or suspended lignocellulosic material, thereby generating (i) a cellulose-rich stream containing precipitated cellulose and (ii) a first intermediate stream comprising the lignin, the solvent for biomass, and the cellulose precipitant;

(d) introducing a lignin precipitant to the intermediate stream, thereby generating (i) a lignin-rich stream containing precipitated lignin and (ii) a second intermediate stream comprising the solvent for biomass, the cellulose precipitant, and the lignin precipitant;

(e) recovering and recycling the solvent for biomass, the cellulose precipitant, and the lignin precipitant from the second intermediate stream;

(f) feeding the cellulose-rich stream into one or more anaerobic digesters operated at effective fermentation conditions to generate methane-containing biogas and a digester slurry; and (g) recovering the methane-containing biogas from the one or more anaerobic digesters.

The solvent for biomass may be selected from the group consisting of acetic acid, phosphoric acid, sulfuric acid, ethanol, and combinations thereof. The cellulose precipitant may be selected from ethers, such as isopropyl ether. The lignin precipitant may be selected from ethers, such as isopropyl ether. Note that the cellulose precipitant may be the same chemical as the lignin precipitant.

In some embodiments, the size-reduced lignocellulosic material further comprises hemicellulose, and the cellulose-rich stream contains precipitated hemicellulose. In these or other embodiments, the lignin-rich stream contains precipitated hemicellulose derived from the size-reduced lignocellulosic material that contains hemicellulose. Optionally, hemicellulose is recovered from the first intermediate stream and/or the second intermediate stream and introduced to one or more anaerobic digesters.

Step (e) of these process variations may include addition of wash water followed by evaporation. Alternatively, or additionally, step (e) may include dewatering in a screw press and/or centrifuge.

The lignin-rich stream may be recovered. In some embodiments, the process further includes adding enzymes to the lignin-rich stream to fractionate lignin by size, thereby generating a plurality of lignin-rich streams.

In some embodiments, one or more lignin-rich streams are combusted to provide energy for the process.

In some embodiments, one or more lignin-rich streams are gasified to provide syngas.

In some embodiments, one or more lignin-rich streams are pyrolyzed to generate a pyrolysis solid phase, a pyrolysis liquid phase, and a pyrolysis gas phase. The process may include feeding a portion of the pyrolysis solid phase to one or more anaerobic digesters or to a post-digester disposed downstream of one or more anaerobic digesters. The digester slurry, a solid portion thereof, and/or a liquid portion thereof may be co-pyrolyzed with the lignin-rich stream.

The process may further include separating the digester slurry into a liquid digestate and a solid digestate. The liquid digestate may be recovered as a first co-product and/or the solid digestate may be recovered as a second co-product.

Yet other variations provide a process for converting a lignocellulosic feedstock into methane, the process comprising:

(a) grinding or milling a lignocellulosic feedstock, to generate a size-reduced lignocellulosic material;

(b) introducing a pretreatment chemical to the size-reduced lignocellulosic material;

(c) pelletizing or extruding the size-reduced lignocellulosic material, to generate a plurality of lignocellulosic pellets or extrudates;

(d) feeding the lignocellulosic pellets or extrudates, or a slurry formed therefrom, into one or more anaerobic digesters operated at effective fermentation conditions to generate methane-containing biogas and a digester slurry;

(e) separating the methane-containing biogas into methane-rich gas and $CO_2$-rich gas;

(f) recovering the methane-rich gas; and (g) recovering or recycling the $CO_2$-rich gas comprising carbon dioxide.

In some embodiments, at least some of the $CO_2$-rich gas is sequestered into a geological formation, such as for underground storage or for enhanced oil recovery at an oil well.

In some embodiments, at least some of the $CO_2$-rich gas is recycled to the one or more anaerobic digesters, wherein hydrogen is introduced to the one or more anaerobic digesters, and wherein the hydrogen and the carbon dioxide react hydrogenotrophically to generate additional methane.

In some embodiments, at least some of the $CO_2$-rich gas is recycled to a hydrolysis unit disposed upstream of the one or more anaerobic digesters, wherein hydrogen is introduced to the hydrolysis unit, and wherein the hydrogen and the carbon dioxide react hydrogenotrophically to generate additional methane.

In some embodiments, at least some of the $CO_2$-rich gas is recycled to a post-digester disposed downstream of the one or more anaerobic digesters, wherein hydrogen is introduced to the post-digester, and wherein the hydrogen and the carbon dioxide react hydrogenotrophically to generate additional methane.

In some embodiments, at least some of the $CO_2$-rich gas is introduced to a catalytic methane-generation reactor, wherein hydrogen is introduced to the catalytic methane-generation reactor, and wherein the wherein the hydrogen and the carbon dioxide react catalytically to generate additional methane.

When external hydrogen is introduced to the process, the external hydrogen may be provided from any source, such as water electrolysis or from gasification of a carbon-containing intermediate material recovered from the process, forming syngas, and capturing the hydrogen from the syngas. The carbon-containing intermediate material may be solid digestate recovered from the digester slurry, or lignin recovered from the process, for example.

Still other variations provide a process for converting a lignocellulosic feedstock into methane, the process comprising:

(a) grinding or milling a lignocellulosic feedstock, to generate a size-reduced lignocellulosic material;

(b) introducing a pretreatment chemical to the size-reduced lignocellulosic material;

(c) pelletizing or extruding the size-reduced lignocellulosic material, to generate a plurality of lignocellulosic pellets or extrudates;

(d) feeding the lignocellulosic pellets or extrudates, or a slurry formed therefrom, into a first anaerobic digester operated at effective acetoclastic fermentation conditions to generate methane-containing biogas and an intermediate digester slurry;

(e) feeding the intermediate digester slurry, hydrogen, and carbon dioxide into a second anaerobic digester operated at effective hydrogenotrophic fermentation conditions to generate additional methane-containing biogas and a digester slurry; and (f) recovering the methane-containing biogas and the additional methane-containing biogas from the first and second anaerobic digesters.

In some embodiments, at least some of the hydrogen is derived from a biological hydrolysis step carried out in a hydrolysis unit disposed upstream of the first anaerobic digester.

In some embodiments, at least some of the hydrogen is generated within the first anaerobic digester.

In some embodiments, at least some of the hydrogen is provided from water electrolysis.

In some embodiments, at least some of the hydrogen is provided from syngas generated from a carbon-containing intermediate material recovered from the process. The carbon-containing intermediate material may be, for example, solid digestate recovered from the intermediate digester slurry and/or from the digester slurry.

The carbon dioxide for step (e) may be derived from a biological hydrolysis step carried out in a hydrolysis unit disposed upstream of the first anaerobic digester.

The carbon dioxide for step (e) may be generated from a solid digestate recovered from the intermediate digester slurry and/or from the digester slurry.

In some embodiments, in step (e), the hydrogen and the carbon dioxide are present at a $H_2/CO_2$ volumetric ratio of about 2 to about 6, such as about 3 to about 5.

In some embodiments, the methane-containing biogas is conveyed to the second anaerobic digester, and both of the methane-containing biogas and the additional methane-containing biogas are recovered from the second anaerobic digester. Heat may be recovered from the second anaerobic digester, and this heat may be reused in the process (e.g., introduced to the first anaerobic digester).

Some specific embodiments are directed to a process for converting a lignocellulosic feedstock into methane, the process comprising:

(a) providing a lignocellulosic feedstock comprising grass straw and wheat straw;

(b) grinding or milling the lignocellulosic feedstock, to generate a size-reduced lignocellulosic material;

(c) introducing potassium hydroxide to the size-reduced lignocellulosic material, thereby generating conditioned lignocellulosic material;

(d) cubing the conditioned lignocellulosic material, to generate a plurality of lignocellulosic cubes;

(e) conveying the lignocellulosic cubes from a first location to a second location within the process;

(f) forming a lignocellulosic slurry by combining (1) the lignocellulosic cubes and (2) a liquid stream comprising water;

(g) feeding the lignocellulosic slurry into a plurality of anaerobic digesters each operated at effective fermentation conditions to generate methane-containing biogas and a digester slurry, wherein the anaerobic digesters each contain thermophilic bacteria, and wherein the effective fermentation conditions include a temperature from 50° C. to 60° C., a pH from 7.2 to 7.9, a residence time from 15 days to 60 days, total suspended solids from 5 wt % to 20 wt %, and organic dry matter content from 60 wt % to 75 wt % of total dry matter;

(h) recovering the methane-containing biogas, directly or indirectly, from the one or more anaerobic digesters;

(i) separating the digester slurry into a liquid digestate and a solid digestate; and (j) recycling at least some of the liquid digestate back to step (d), step (f), and/or step (g).

In some embodiments, the size-reduced lignocellulosic material has an average maximum particle size of about 1 inch or less.

In some embodiments, a waste feedstock is also fed to the one or more anaerobic digesters, wherein the waste feedstock is selected from the group consisting of food waste, agricultural organic waste, industrial organic waste, livestock manure, and combinations thereof. The weight ratio of the lignocellulosic feedstock to the waste feedstock may be selected from about 0.3 to about 3.0.

The potassium hydroxide may be present in a concentration from about 0.1 wt % to about 1 wt % based on the dry-basis weight of the conditioned lignocellulosic material.

Steps (b) and (c) may be performed simultaneously.

The lignocellulosic cubes may have an average minimum length scale selected from about 0.5 inch to about 2 inches, and an average maximum length scale selected from about 1 inch to about 6 inches. Step (d) may include cubing at a pelletizing temperature selected from about 50° C. to about 100° C.

In some embodiments, the process further comprises a hydrolysis step including hydrolysis of the lignocellulosic slurry, prior to step (g). The hydrolysis step may include enzymatic hydrolysis assisted with micro-aeration of the lignocellulosic slurry.

In some embodiments, the process further comprises recycling the digester slurry, or a solid digestate derived therefrom, back to the hydrolysis step.

The methane-containing biogas may be purified to generate an upgraded biogas with higher methane content compared to the methane-containing biogas. For example, the upgraded biogas may contains at least 97 vol % methane, or other suitable concentration of pipeline-quality cellulosic methane.

At least some of the liquid digestate may be recovered as a co-product selected from the group consisting of a fuel, biochar, pyrolysis oil, soil conditioner, agricultural fertilizer, organic soil product, soil enhancement material, landfill conditioner, and combinations thereof. In certain embodiments, at least some of the liquid digestate is recovered as a fine-particles slurry containing from about 1 wt % to about 10 wt % total solids, from about 0.2 wt % to about 4 wt % nitrogen (elemental N basis), from about 0.05 wt % to about 2 wt % phosphorous (element P basis), and from about 0.1 wt % to about 2 wt % potassium (element K basis).

At least some of the solid digestate may be recovered as a co-product selected from the group consisting of a solid fuel, biochar, pyrolysis oil, soil conditioner, agricultural fertilizer, organic soil product, soil enhancement material, landfill conditioner, and combinations thereof. In certain embodiments, at least some of the solid digestate is recovered as a fibrous humid cake containing from about 10 wt % to about 50 wt % total solids, from about 0.1 wt % to about 2 wt % nitrogen (elemental N basis), from about 0.1 wt % to about 3 wt % phosphorous (element P basis), and from about 0.05 wt % to about 1 wt % potassium (element K basis). In certain embodiments, some or all of the solid digestate is composted.

Related embodiments provide a system configured to carry out a process as disclosed. Related embodiments provide a methane product produced by a process as disclosed.

BRIEF DESCRIPTION OF THE DRAWINGS

In the attached drawings (FIGS. 1 to 20), dotted or dashed lines denote optional inputs and streams.

DETAILED DESCRIPTION OF EMBODIMENTS

Figure 1:
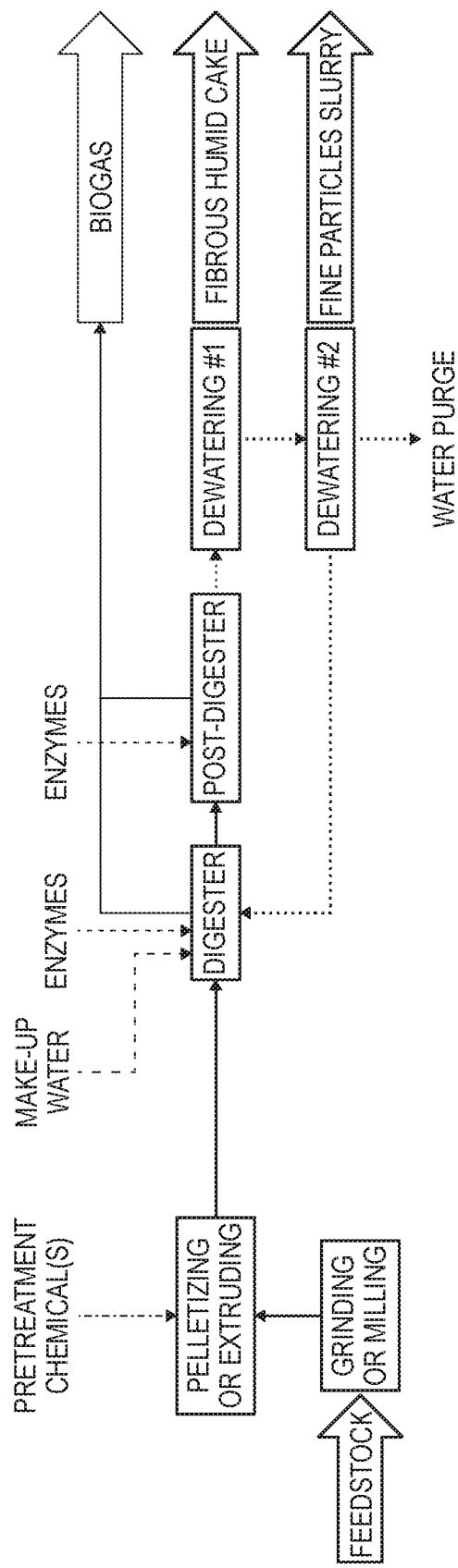
FIG. 1 depicts an exemplary anaerobic digestion process and system, in which incoming lignocellulosic feedstock is converted to biogas, fibrous humid cake, and a fine-particles slurry.

The processes, systems, methods, materials, and compositions of the present disclosure will be described in detail by reference to various non-limiting embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except when used in Markush groups. Thus in some embodiments not otherwise explicitly recited, any instance of "comprising" may be replaced by "consisting of" or, alternatively, by "consisting essentially of."

The present invention, in some embodiments, is premised on improved processes and systems for anaerobic digestion of one or more carbon-containing feedstocks into biogas and potentially co-products.

In some variations, a process is provided for converting a lignocellulosic feedstock into methane, the process comprising:

(a) grinding or milling a lignocellulosic feedstock, to generate a size-reduced lignocellulosic material;

(b) introducing a pretreatment chemical to the size-reduced lignocellulosic material;

(c) pelletizing or extruding the size-reduced lignocellulosic material, to generate a plurality of lignocellulosic pellets or extrudates;

(d) feeding the lignocellulosic pellets or extrudates, or a slurry formed therefrom, into one or more anaerobic digesters operated at effective fermentation conditions to generate methane-containing biogas and a digester slurry; and (e) recovering the methane-containing biogas from the one or more anaerobic digesters.

The lignocellulosic feedstock contains at least cellulose and typically contains lignin. The processes and systems of the invention can accommodate a wide range of feedstocks of various types, sizes, and moisture contents. For example, biomass such as agricultural wastes, forest products, grasses, and other cellulosic material may be used. In various embodiments, the lignocellulosic feedstock includes one or more materials selected from grass straw, corn stover, wheat straw, rice straw, cotton burr, sugarcane bagasse, switchgrass, *miscanthus*, animal manure, municipal garbage, municipal sewage, commercial waste, grape pumice, almond shells, pecan shells, coconut shells, coffee grounds, grass pellets, hay pellets, wood pellets, timber harvesting residues, softwood chips, hardwood chips, tree branches, tree stumps, leaves, bark, sawdust, paper, cardboard, or off-spec paper pulp. A person of ordinary skill in the art will appreciate that the feedstock options are virtually unlimited. In certain embodiments, the lignocellulosic feedstock is selected from the group consisting of grass straw, wheat straw, corn stover, grain straw, rice straw, cotton burr, sugarcane bagasse, and combinations thereof.

Grinding or milling in step (a) reduces the incoming particle size of the lignocellulosic feedstock so that it can be processed with higher efficiency. Many types of lignocellulosic feedstock are harvested as long pieces of material, such as several feet in length. It is beneficial to reduce the average maximum particle size of the lignocellulosic material to less than 6 inches, more preferably less than 3 inches, and most preferably about 1 inch or less. In some embodiments, grinding or milling also increases the surface area of the lignocellulosic feedstock particles.

Grinding or milling in step (a) may be carried out using known apparatus, such as (but not limited to) hammer mills, duplex mills, shredders, Valley beaters, single disk refiners, double disk refiners, conical refiners, cylindrical refiners, homogenizers, microfluidizers, or sonicators, to generate a size-reduced lignocellulosic material.

Classifying equipment may be incorporated into the grinding or milling step, to separate the lignocellulosic feedstock particles as a function of their size. Classifying systems select those particles whose size satisfies the final requirement (e.g., about 1 inch or less). Classifiers may be used as a final stage or as an intermediate stage to convey coarse particles again to the grinder or mill (recirculation flow). When the upper limit size is fixed, coarse particle may be eliminated or may be passed by the mill a number of times necessary to obtain the desired particle size.

In various embodiments, the size-reduced lignocellulosic material has an average maximum particle size (e.g., length) of about 2, 1.5, 1.4, 1.3, 1.2, 1.1, 1.0, 0.9, 0.8, 0.7, 0.6, 0.5, 0.2, or 0.1 inches. It is possible to mill the lignocellulosic feedstock down to fine particles with less than 0.1 inch in diameter, or even a flour with less than 0.01 inch in diameter, but the processing energy cost associated with generating fine particles and especially a flour is typically high.

Note that in some embodiments, a size-reduced lignocellulosic material is received at a manufacturing facility such that there is no requirement for further size reduction. This situation may arise, for example, when the location of grinding or milling is different than the location of the rest of the process, steps (b) to (e). The entity carrying out step (a) may be different than the entity carrying out steps (b) to (e). Also, certain feedstocks may naturally be of adequately small dimensions so that grinding or milling is not necessary. For example, waste paper may only need to be slurried and not further ground or milled. Another example is corn stover pith and similar fine particles of agricultural residues, which generally are small particles (dust-like) and may not need to be ground or milled.

In some variations, a waste feedstock is also fed to the one or more anaerobic digesters. Waste feedstocks may be selected from food waste, agricultural organic waste, industrial organic waste, livestock manure, or a combination thereof, for example. A waste feedstock may or may not contain cellulose and/or lignin. Cow manure, for example, contains cellulose and lignin that is not digested. Certain food wastes may contain high amounts of oils and/or starches but contain substantially no cellulose or lignin.

When both a lignocellulosic feedstock and a waste feedstock are utilized in the same process, the two feedstocks may be fed to the same anaerobic digester or, more typically, to different anaerobic digesters that can be separately optimized for the different types of feedstocks. When both a lignocellulosic feedstock and a waste feedstock are utilized, the weight ratio of the lignocellulosic feedstock to the waste feedstock may be selected from about 0.3 to about 3.0, such as about 1.0 or about 2.0. The feedstock ratio may vary over time depending on the dynamic feed input to the process.

The pretreatment chemical in step (b) may be selected to alter the chemical properties of the lignocellulosic feedstock, the physical properties of the lignocellulosic feedstock, or both of these. For example, the pretreatment chemical may act as a reactant or a catalyst for a reaction that cracks the structure of the lignocellulosic feedstock, increasing reactivity toward enzymes or microorganisms downstream in the process. The pretreatment chemical may be selected primarily for breaking up of cellulose and/or hemicellulose polymers to reduce their molecular weights. Alternatively, or additionally, the pretreatment chemical may be selected to enhance the pelletizing or extruding in step (c), such as by improving particle bonding to enhance mechanical integrity or breaking particle bonding to allow for enhanced impact of the bacterial access in subsequent biological degradation steps (hydrolysis and/or digester).

The pretreatment chemical may be an acid, a base, a salt, or a solvent, for example. In some embodiments, the pretreatment chemical is selected from the group consisting of sodium hydroxide, potassium hydroxide, calcium carbonate, ammonia, acetic acid, phosphoric acid, urea, carbon dioxide, salts of any of the foregoing, and combinations thereof, for example.

The pretreatment chemical may be present in a concentration from about 0.1 wt % to about 10 wt % based on the combined weight of the size-reduced lignocellulosic material and the pretreatment chemical, on a dry basis (i.e. not including water that is present). In various embodiments, the pretreatment chemical is present in a concentration of about 0.5 wt %, 1 wt %, 2 wt %, 5 wt %, or 10 wt %, based on the combined weight of the size-reduced lignocellulosic material and the pretreatment chemical, on a dry basis.

In some embodiments, steps (a) and (b) are carried out simultaneously. In these embodiments, a pretreatment chemical is fed directly into an apparatus for grinding or milling, i.e. the pretreatment chemical is introduced to a feedstock as it is being ground or milled. The pretreatment chemical may be introduced to the ground or milled feedstock directly as it leaves the grinding or milling apparatus, or the pretreatment chemical may be added downstream and/or at a later time (such as in a batch-wise process).

In principle, step (b) may be carried out prior to step (a). That is, the pretreatment chemical may be introduced to the starting feedstock prior to being ground or milled. Depending on the selection of pretreatment chemical, this embodiment may lead to corrosion in the grinding or milling apparatus. On the other hand, a pretreatment chemical in the form of a salt, for example, may actually enhance the grinding or milling efficiency.

In step (c), mechanical force is applied to the size-reduced lignocellulosic material, to generate pellets or extrudates. An "extrudate" refers to a product from an extrusion step. Pelletizing utilizes mechanical forces and may form new chemical bonds between lignocellulosic fibers or within the fibers. Extrusion imposes high mechanical forces, preferably longitudinal shear forces into the lignocellulosic material, enhancing the surface of the material and allowing for a higher impact/effect of bacteria, enzymes, and/or chemicals added in subsequent steps, leading ultimately to a higher biogas production from the material. Steps (a) and (c), taken together, are a type of mechanical pretreatment.

Compression of lignocellulosic material solves the problem described in the Background regarding distribution of dry lignocellulosic feedstock into liquids of process tanks. By compressing the lignocellulosic feedstock into pellets, several effects are beneficial for the downstream process.

First, the densification of the lignocellulosic feedstock into pellets (e.g., cubes) reduces feedstock volumes and increases density significantly, which enhances process efficiency.

Second, compressed pellets can easily be transported by conveyors and elevators over long distances, as known from the timber wood pellet industry, for example.

Third, compressed pellets can much more easily be fed into process tanks containing liquids, compared to loose lignocellulosic feedstock.

Fourth, compressed pellets—due to their enhanced density compared to loose biomass—do not normally form floating layers in liquid process tanks, but rather allow for a good distribution of the fed biomass into the liquid of a process tank.

Fifth, compressed pellets or extrudates can also be easily fed into screw pump systems known in the industry (e.g., Bio-Mix pumps from Wangen America Inc., Wood Dale, Ill., USA), which mix liquids and biomass to form a slurry that is pumped forward. If loose, low-density biomass is instead fed into such a pump, the intake capacity of the pump in terms of dry matter per hour would be much lower compared to feeding the pump with densified pellets or extrudates.

Sixth, once the compressed pellets are fed into a liquid environment or a liquid tank, the pellets start mechanically disintegrating, generally within about 10 minutes to about 2 hours, such as from about 30 minutes min to about 1 hour. The mechanical disintegration leads to a homogenous distribution of lignocellulosic biomass within the liquid of the process tank.

An additional effect of compressing the biomass into pellets or extruding the biomass is the increase of temperature of the biomass. The temperature may be adjusted by the flow rate of biomass into the pelletizing machine or extruder, and by the compression rate. For pelletizing, typically temperatures between 30-90° C. are achieved, wherein a temperature between 50-80° C. is favorable. This increase of temperature and pressure results in the formation of stable pellets that can easily be transported mechanically by conveyors without disintegrating or crumbling.

Due to high friction and pressure imposed by the extruder on the lignocellulosic material, extrusion of biomass increases the temperature inside the material significantly (preferably to temperatures of about 70-120° C.) and results in the evaporation of water contained in the fed material and the formation of steam. This environment of pressure, temperature, and steam during the extrusion process causes a beneficial change of the consistency and characteristic of the lignocellulosic material and makes the material more receptive for the beneficial effects of bacterial, chemical, and/or enzymatic impacts in subsequent stages.

During the discharge of the pressurized material at the outlet of the extrusion step into the ambient atmosphere, the rapid pressure drop to ambient pressure causes partial steam explosions in the lignocellulosic material, which again support the disruption of the lignocellulosic fiber structure of the biomass for better bacterial, enzymatic or chemical access in subsequent process stages.

The shape of lignocellulosic pellets may vary widely. In various embodiments, lignocellulosic pellets may be in the form of spheres or sphere-like objects (e.g., ellipsoids), cylinders, rods, cubes, rings, disks, or random shapes. The lignocellulosic pellet may be in the form of a lignocellulosic briquette, which may take the shape of a conventional charcoal briquette, for example.

In some embodiments, the lignocellulosic pellets or extrudates are in the form of lignocellulosic cubes. In this disclosure, a "cube" refers to a three-dimensional shape with all three dimensions the same or approximately the same (such as within 10%), as well as to a cuboid (rectangular prism). A cuboid is a box-shaped object in which all faces are rectangles. A cuboid is a rectangular prism because it has the same cross-section along a length. A cuboid is essentially a cube that is elongated in one dimension. For example, a cuboid may have a cross-section that is a square with sides of about 1 inch, and an overall length that is greater than 1 inch, such as 2 inches, 3 inches, or 6 inches.

In some embodiments employing lignocellulosic cubes, the lignocellulosic cubes have an average minimum length scale selected from about 0.1 inch to about 6 inches, such as an average minimum length scale selected from about 0.5 inch to about 2 inches. In these or other embodiments, the lignocellulosic cubes have an average maximum length scale selected from about 0.5 inch to about 12 inches, such as an average maximum length scale selected from about 1 inch to about 6 inches.

When step (c) includes pelletizing, the pelletizing may be conducted at a pelletizing temperature selected from about 25° C. to about 150° C., such as from about 50° C. to about 100° C. In some embodiments, a pelletizing temperature from about 50° C. to about 80° C. is favorable for producing pellets. Pelletizing at a temperature higher than ambient temperature (e.g. 25° C.) enhances the formation of a stable pellet, via thermally activated chemical reactions and/or increased mass transport of lignin that acts as an internal glue for the pellet. The pelletizing temperature may be controlled via external heat exchangers, which may be configured to heat or cool the pelletizing region. Note that the mechanical energy for pelletizing will generally raise the internal pellet temperature. The internal pellet temperature will depend on the initial temperature of feed material, the rate of pelletizing, the size of pellets, and any heating or cooling that is carried out during pelletizing. Following formation of pellets, the pellets may be allowed to cool to ambient temperature before further processing. The bulk density of the pellets is generally from about 20 lb/ft$^3$ to about 40 lb/ft$^3$, such as about 25-30 lb/ft$^3$.

As noted above, an extrusion step may be applied as an alternative to compression of lignocellulosic feedstock into pellets. Extrusion is a mechanical technique wherein a biomass material is mechanically crushed through an extruder. By passing through the extruder, the lignocellulosic material is crushed into fibers, increasing the accessible surface area of the lignocellulosic material.

As the lignocellulosic material moves forward through the extruder, the pressure and temperature increases, up to typically 5-15 bar and 160-180° C., respectively. When the lignocellulosic material exits the extruder, the pressure and temperature drop quickly, in essentially the same way as in steam explosion. Thus, the advantages of extrusion are to some extent similar to those in steam explosion of lignocellulosic material.

The diameter and length of the screws have a significant impact on the extrusion stability and shearing forces. In some embodiments, extrusion process stability and high shearing forces are provided by two counter-rotating screws with screw diameter each greater than about 4 inches, preferably greater than about 16 inches. Screw diameters greater than about 4 inches allow long, fibrous biomass to be processed without clogging the entrance of the extruder. The screw length to screw diameter ratio of the screws may be up to 30 and is preferably about 5 or less, more preferably about 1, to avoid choking or wear and tear of the extrusion system. In some embodiments, the extruder is a 2-shaft extrusion machine such as a PES extruder from Promeco SpA (Fino Mornasco, Italy).

It is well-known in the biorefinery art that accessible surface area of biomass is positively correlated to effectiveness of enzymatic hydrolysis. Therefore, increasing the surface area of biomass would be beneficial for downstream processing of lignocellulosic feedstock. Tests by the present inventors have shown that an extruder increases the surface area of the biomass being extruded.

In particular, the extruder affects the structure of the fed biomass in such way that the lignocellulosic structure is mechanically and/or thermally broken up. The environment of high mechanical shear forces, high temperature, and relatively high pressure causes disintegration of the lignocellulosic structure, which in turn accelerates the hydrolysis of the biomass and increases the biogas production during anaerobic digestion in one or more process units.

An additional effect that arises in some embodiments is that during the ejection of extruded material out of the extruder exit slots, an immediate pressure drop occurs from the high-pressure environment inside the extruder barrel down to normal atmospheric pressure outside the extruder. This abrupt pressure drop causes steam explosion of the extrudate, which further contributes to disruption of the lignocellulosic structure and leads to faster biogas production, and higher biogas yields, in the subsequent process units.

In some embodiments, water or an aqueous liquid (e.g., liquid digestate) is added onto the extruder feed material, prior to feeding to the extruder, or directly adding such water or aqueous liquid via an inlet port into the extruder. Due to the temperature increase inside the extruder barrel, the added water partially evaporates and the created steam contributes to a further increase of pressure inside the extruder barrel, followed by a sudden pressure reduction and steam explosion of the extruded biomass.

Another benefit of extrusion, in some embodiments, is that the surface structure of the extruded biomass is altered (mechanically, thermally, chemically, or a combination thereof) such that the hydrophobicity is reduced. With reduced hydrophobicity, the extruded material is more mixable into liquid processes and tanks, without having the problem of creating floating layers inside such tanks, and without the problem of a heterogeneous mixture of biomass inside a liquid tank.

The bulk density of the extruded biomass is increased significantly, compared to the extruder feed material. The densification into extrudates enables more efficient transport and feed rates downstream of the extruder. The extruded biomass, in some embodiments, exhibits characteristic similar to corn silage and shows favorable behavior when being subsequently mixed into liquid processes and tanks, thus avoiding floating layers or heterogeneous distribution within a subsequent liquid process tank.

When step (c) includes extruding, the lignocellulosic extrudates may be in any of the aforementioned size ranges, or other sizes. In some embodiments, long extrudates are formed before cutting them into rods or other geometries. The lignocellulosic extrudates may be continuously or intermittently cut into objects with an average minimum length scale selected from about 0.1 inch to about 6 inches, and/or an average maximum length scale selected from about 0.5 inch to about 12 inches, for example. In some embodiments, the material exiting the extruder is exploded when exposed to atmospheric pressure, resulting in a material with a maximum dimension that is less than 1 inch, less than 0.5 inches, less than 0.2 inches, or less than 0.1 inches, for example.

Extrusion may be conducted at an extrusion temperature selected from about 50° C. to about 250° C., such as from about 100° C. to about 200° C., for example. In some embodiments, an extrusion temperature from about 160° C. to about 180° C. is favorable for producing extrudates. Extruding at a temperature of at least 50° C. enhances the disruption of the lignocellulosic matrix. The extrusion temperature may be controlled via external heat exchangers, which may be configured to heat or cool one or more zones of the extruder. The mechanical energy for extrusion will raise the internal temperature of the material being extruded. The internal temperature will depend on the initial temperature of feed material, the flow rate of extrusion, the extruder screw dimensions, and any heating or cooling that is carried out during extrusion. Following formation of extrudates, they may be allowed to cool to ambient temperature before further processing.

The extruder may be a single-screw extruder, a double-screw extruder (also known as a twin-screw extruder), or another type of extruder. In some embodiments, the lignocellulosic extrudates are formed in a double-screw extruder. The double-screw extruder may be configured with two co-rotating screws or two counter-rotating screws. In certain embodiments, two counter-rotating screws are employed, with each extruder screw having an average screw diameter of at least about 4 inches, at least about 8 inches, at least about 12 inches, or at least about 16 inches. In certain embodiments, two counter-rotating screws each have a ratio of screw length to screw diameter less than 5, less than 4, less than 3, less than 2, about 1.5, or about 1.0.

The addition of a pretreatment chemical supports the opening and weakening of the lignocellulosic matrix of the feedstock, resulting in higher yields of biogas in subsequent fermentation. Preferably, the pretreatment chemical is added to the lignocellulosic feedstock shortly before feeding it into the compression machine. Other times or locations of adding the pretreatment chemical are possible. The pretreatment chemical may be introduced such as by dosing or spraying on a biomass in-feed transport conveyor, or by adding the pretreatment chemical through dosing or liquid nozzles directly into the pelletizer or extruder, for example. Due to the high pressure (via compression) and increased temperature (as discussed above), the effect of the added pretreatment chemical on weakening the lignocellulosic matrix is favorably increased, and the consumption of pretreatment chemical is reduced compared to adding the pretreatment chemical without a compression stage.

Process steps (b) and (c) may be performed simultaneously. In these embodiments, the pretreatment chemical may be added directly to a pelletizing apparatus or an extruder. In the case of a pelletizing apparatus, the pretreatment chemical may be co-fed along with size-reduced lignocellulosic material, or may be continuously fed in another port, for example. In the case of an extruder, the pretreatment chemical may be fed (relative to the size-reduced lignocellulosic material) co-currently, counter-currently, or via side ports in the extruder.

In certain embodiments, step (b) is conducted following step (c). That is, the pretreatment chemical may be introduced to a lignocellulosic pellet or extrudate after it has been formed. Various combinations are possible. For example, a first amount of pretreatment chemical may be added to the size-reduced feedstock prior to pelletizing or extrusion, and then a second amount of pretreatment chemical may be added to the pellets or extrudates. Or, a pretreatment chemical added to the size-reduced feedstock may be different than a pretreatment chemical added to the pellets or extrudates.

An advantage of forming lignocellulosic pellets or extrudates is that such objects may be conveyed within the process more conveniently and efficiently than conveying low-density biomass. In some embodiments, lignocellulosic pellets or extrudates are conveyed from a first location to a second location within the process. The first location may be an outlet of a pelletizing apparatus or an extruder, and the second location may be an inlet to an anaerobic digester, a hydrolysis unit, or a slurry tank, for example.

In some embodiments, step (d) comprises forming a slurry from at least some of the lignocellulosic pellets or extrudates, and then feeding the slurry into one or more anaerobic digesters. A slurry is formed by mixing lignocellulosic pellets or extrudates with water or a liquid (e.g., liquid digestate) containing water. Such a slurry may be formed in a mixing tank or a hydrolysis unit disposed upstream of the anaerobic digesters, for example. The conditions to form a slurry from the lignocellulosic pellets or extrudates may vary. Generally, a suitable residence time in a liquid tank is about 30 minutes to about 1 hour, at a temperature from about 25° C. to about 100° C.

Alternatively, or additionally, step (d) may comprise feeding at least some of the lignocellulosic pellets or extrudates directly into one or more anaerobic digesters. Within the anaerobic digesters, the lignocellulosic pellets or extrudates typically form a slurry prior to, or during, fermentation (anaerobic digestion).

In some embodiments, the process further comprises a hydrolysis step including (i) hydrolysis of the size-reduced lignocellulosic material and/or (ii) hydrolysis of a slurry formed from the lignocellulosic pellets or extrudates, prior to step (d). The hydrolysis step is carried out in a hydrolysis unit. Hydrolysis may be enzymatic hydrolysis, when suitable enzymes are introduced to the hydrolysis unit. Suitable enzymes may include cellulases, hemicellulases, and/or ligninases which may cause molecular-weight reduction of cellulose, hemicellulose, and lignin, respectively, or other chemical reactions including generation of $CH_4$, CO, $CO_2$, and/or $H_2$ from the lignocellulosic pellets or extrudates. In some embodiments, enzymes introduced or present in the hydrolysis unit include endoglucanases and exoglucanases. Endoglucanases are cellulases that attack low-crystallinity regions in the cellulose fibers by endoaction, creating free chain-ends. Exoglucanases or cellobiohydrolases are cellulases that hydrolyze the 1,4-glycocidyl linkages in cellobiose.

Cellulases may include β-glucosidases that convert cellooligosaccharides and disaccharide cellobiose into glucose. There are a number of enzymes that can attack hemicelluloses, such as glucoronide, acetylesterase, xylanase, β-xylosidase, galactomannase, and glucomannase.

Various enzymes may be utilized, such as one or more enzymes recited in Verardi et al., "Hydrolysis of Lignocellulosic Biomass: Current Status of Processes and Technologies and Future Perspectives," Bioethanol, Prof. Marco Aurelio Pinheiro Lima (Ed.), ISBN: 978-953-51-0008-9, InTech (2012), which is hereby incorporated by reference.

Some embodiments employ thermotolerant enzymes obtained from thermophilic microorganisms. The thermophilic microorganisms can be grouped in thermophiles (growth up to 60° C.), extreme thermophiles (65-80° C.) and hyperthermophiles (85-110° C.). The unique stability of the enzymes produced by these microorganisms at elevated temperatures makes them valuable for processes at harsh conditions. The utilization of high operation temperatures, which cause a decrease in viscosity and an increase in the diffusion coefficients of substrates, may have a significant influence on the cellulose solubilization. Most thermophilic cellulases do not show inhibition at high levels of reaction products (e.g. cellobiose and glucose). As a consequence, higher reaction rates and higher process yields are expected. The high process temperature also reduces contamination.

In some embodiments, an enzyme is selected such that at a high temperature, the enzyme is able to catalyze liquefaction (partial hydrolysis) but not saccharification (total hydrolysis). In some processes, a hydrolysis unit is configured to cause at least some liquefaction as a result of enzymatic action on biomass. "Liquefaction" means partial hydrolysis of cellulose to form glucose oligomers (i.e. glucan) that dissolve into solution, but not total hydrolysis of cellulose to glucose monomers (saccharification). The glucose oligomers may then be digested by microorganisms to generate biogas. In some embodiments, a hydrolysis unit is configured for saccharification, generating monomers which are then digested to form biogas.

In alternative embodiments, acid-catalyzed hydrolysis (e.g., with sulfuric acid) or base-catalyzed hydrolysis (e.g., with sodium hydroxide) may be carried out, without enzymes.

The hydrolysis step may be conducted at a hydrolysis temperature selected from about 50° C. to about 70° C., for example. The hydrolysis step may be conducted at a hydrolysis pH selected from about 4 to about 10, such as from about 6 to about 8, for example. The hydrolysis step may be conducted at a hydrolysis residence time selected from about 4 hours to about 7 days, such as from about 12 hours to about 2 days. In some embodiments, a digester slurry, or a solid digestate derived therefrom (e.g. following solid/liquid separation of the digester slurry), is recycled back to the hydrolysis unit.

Optionally, the hydrolysis step may be assisted with micro-aeration of the size-reduced lignocellulosic material and/or the slurry formed from the lignocellulosic pellets or extrudates. Micro-aeration may be accomplished by introducing relatively small amounts of oxygen, air, or oxygen-enriched air into the hydrolysis unit. In some embodiments, minor amounts of oxygen that is dissolved or entrained in the material being processed is sufficient for micro-aeration, without the requirement for a dedicated input of a micro-aeration gas.

Anaerobic digesters can be designed and engineered to operate using a number of different configurations and can be categorized into batch vs. continuous process mode, mesophilic vs. thermophilic temperature conditions, high solids vs. low solids, and single stage vs. multistage processes.

In a batch system, biomass is added to the reactor (anaerobic digester) at the start of the process. The reactor is then sealed for the duration of the process. In its simplest form, batch processing utilizes inoculation with already processed material to start the anaerobic digestion. In continuous digestion processes, organic matter is constantly added or is added at multiple times to the reactor. Here, the end products are constantly or periodically removed, resulting in constant production of biogas. Examples of this form of anaerobic digestion include continuous stirred-tank reactors, upflow anaerobic sludge blankets, expanded granular sludge beds, and internal circulation reactors. Fed-batch anaerobic digestion is also possible, in which feedstock is continuously fed but product biogas is not removed until the end of the batch process.

The effective fermentation conditions in the anaerobic digesters are conditions that generate at least some methane-containing biogas from the input material. Different anaerobic digesters may be operated with different conditions, or all the anaerobic digesters may be operated under substantially the same conditions.

Effective fermentation conditions may include a fermentation temperature selected from about 20° C. to about 70° C., such as about 50° C. to about 60° C., for example. In various embodiments, the fermentation temperature may be about 40° C., about 45° C., about 50° C., about 55° C., about 60° C., or about 65° C. The fermentation temperatures for anaerobic digesters are preferably selected based on the species of methanogens (or other microorganisms) in the digesters. Mesophilic digestion takes place at temperatures from about 20° C. to about 45° C., such as about 30° C. to about 38° C., when mesophilic microorganisms are present. Thermophilic digestion takes place from about 50° C. to about 60° C., or at elevated temperatures up to about 70° C., when thermophilic microorganisms are present. Thermophilic temperatures enhance the disintegration and gas production from the feedstock.

Effective fermentation conditions therefore may include presence of a thermophilic microorganism, a mesophilic microorganism, or both types of microorganisms. Microorganisms are typically bacteria but may be yeasts. Exemplary microorganisms include, but are not limited to, *Clostridium* species, *Pseudomonas* species, *Eubacterium* species, Mathenaosarcina species, *Methanosaeta thermophila* species, *Methanosaeta concilii* species, and *Methanobacterium* species.

The residence time in a digester varies with the amount and type of feed material and with the configuration of the digestion system. Effective fermentation conditions may include a fermentation time selected from about 5 days to about 60 days, such as about 10 days, about 20 days, about 30 days, about 40 days, or about 50 days. In a typical two-stage mesophilic digestion, residence time varies between about 10 to 60 days, while for a single-stage thermophilic digestion, residence times is normally faster such as about 5 to 40 days.

Effective fermentation conditions may include total suspended solids from about 1 wt % to about 40 wt %, such as from about 5 wt % to about 20 wt %. The total suspended solids is calculated as all solids contained in suspension, but not in solution (e.g., dissolved salts are in solution), divided by total weight in the digester, including all water. High-solids digesters, also known as dry digesters, are designed to process materials with a solids content between about 25 wt % and 40 wt %. Wet digesters can be designed to operate either with high solids content, with a total suspended solids concentration greater than 20 wt %, or low solids content, with a total suspended solids concentration less than 20 wt % (e.g., about 10-15 wt %). In various embodiments, the total suspended solids content is about 5, 10, 15, 20, 25, 30, 35, or 40 wt % in the digester.

The total suspended solids may further be characterized by its organic dry matter content. In some embodiments, the organic dry matter content is from about 30 wt % to about 90 wt % of the total suspended solids, such as about 40 wt %, about 50 wt %, about 60 wt %, about 70 wt %, or about 80 wt %.

Effective fermentation conditions may include a fermentation pH selected from about 6.5 to about 8.5, such as from about 7.0 to about 8.0, for example. In various embodiments, the fermentation pH may be about 6.8, 6.9, 7.0, 7.1, 7.2, 7.3, 7.4, 7.5, 7.6, 7.7, 7.8, 7.9, 8.0, 8.1, or 8.2.

Effective fermentation conditions may include the presence of enzymes to enhance the degradation rate of cellulose, hemicellulose, and/or lignin. For example, cellulases, hemicellulases, and/or ligninases may be introduced to an anaerobic digester, either directly or indirectly (e.g. enzymes may be conveyed from an upstream hydrolysis unit). In some embodiments, a post-digestion step is carried out in one or more post-digesters, into which enzymes may be added to enhance the degradation rate of residual lignocellulosic fibers.

The number of anaerobic digesters may vary, depending on overall desired throughput of the process and the size of each anaerobic digester. Some embodiments employ a single anaerobic digester. Other embodiments employ a plurality of anaerobic digesters, such as 2, 3, 4, 5, 6, 7, 8, 9, 10 or more anaerobic digesters. The anaerobic digesters may be operated in parallel, in series, or a combination thereof. When multiple types of feedstocks are utilized, each feedstock may be fed to one or more anaerobic digesters.

This specification hereby incorporates by reference Taricska et al., "Anaerobic Digestion" In: *Biosolids Treatment Processes. Handbook of Environmental Engineering*, vol 6. Humana Press, 2007 for its teachings of the design and operation of anaerobic digesters, in some embodiments (without limitation).

The methane-containing biogas generated in the anaerobic digesters may be recovered directly from the anaerobic digesters, or may be recovered indirectly, such as by first conveying the methane-containing biogas to another unit, and then capturing the methane-containing biogas from that unit. The other unit may be a post-digester or another reactor, tank, pipe, or sub-system that is designed specifically for recovering methane-containing biogas.

The methane-containing biogas may be recovered in a variety of ways. In some embodiments, the methane-containing biogas is recovered by continuously or periodically sweeping the vapor space of a reactor or tank, using vacuum extraction or a sweep gas, for example. The sweep gas may be recirculating methane-rich gas to avoid diluting the product biogas.

In some embodiments, a double membrane roof is utilized for recovery of the methane-containing biogas. In these embodiments, the biogas produced is channeled out of an anaerobic digester, post-digester, and/or digestate storage tank, through a gas holder double membrane roof, and conveyed to further gas processing (e.g. desulfurization and cooling). The biogas which is temporarily stored in the gasholder roofs flows out by a series of blowers.

In some exemplary embodiments, the methane-containing biogas contains from about 0.1 vol % to about 50 vol % methane, from about 50 vol % to about 99 vol % carbon dioxide, and the remainder water, hydrogen, ammonia, hydrogen sulfide, and other trace gases. In some embodiments, the methane-containing biogas contains from about 0.1 vol % to about 5 vol % hydrogen, from about 0.01 vol % to about 2 vol % ammonia, and from about 0.0001 vol % to about 0.1 vol % hydrogen sulfide, for example.

The methane-containing biogas may be purified to generate an upgraded biogas with higher methane ($CH_4$) content compared to the methane-containing biogas. Methane concentration is increased by removing non-methane components, such as carbon dioxide, water, and sulfur-containing species (e.g., $H_2S$).

For example, after collecting the biogas from the anaerobic digesters and any other units in which biogas is significantly produced, the biogas may be treated in a biogas upgrading system. Preferably, water is condensed out of the biogas stream, to form a dried biogas. Preferably, carbon dioxide is removed from the biogas, using known methods such as amine scrubbing. Preferably, sulfur compounds are removed from the biogas, using known desulfurization methods such as absorption with activated carbon. In addition to adjustment of methane concentration, the biogas upgrading system is preferably capable of adjusting the pressure and temperature of the biogas, tailored for the specific biogas use intended. The biogas may be analyzed and if it does not meet specifications, may be returned to the upgrading system for more treatment.

In various embodiments, the upgraded biogas contains at least 80, 85, 90, 91, 92, 93, 94, 95, 96, 97, 98, or 99 vol % methane. The desired methane concentration in the biogas will generally depend on the intended use of the biogas. The upgraded biogas may have less than 0.1 vol % $CO_2$ and less than 0.9 vol % other gases, in certain embodiments.

The methane-containing biogas, or an upgraded form thereof, may be stored, sold, used, or further treated. In various embodiments, the methane-containing biogas is stored, sold, or used as a gaseous fuel, a liquid fuel, renewable compressed or liquefied natural gas, or cellulosic methane. In some embodiments, the methane-containing biogas is of sufficient quality for direct introduction into a natural gas pipeline.

The methane-containing biogas may alternatively, or additionally, be converted to another product, either onsite or at another location. Any known product from methane may be generated, including (but not limited to) dimethyl ether, syngas, hydrogen, carbon monoxide, or a combination thereof. The methane-containing biogas may be chemically converted to a product, such as via catalytic reactions (e.g., partial oxidation using Pt-based catalysts to generate syngas), or may be biologically converted to a product, such as via methanotrophic fermentation to generate biopolymers and proteins, for example.

When the methane-containing biogas contains carbon dioxide, as is typical, the carbon dioxide may be separated and recovered (rather than being primarily emitted to the atmosphere). The recovered $CO_2$ has many potential uses. In some embodiments, at least some of the recovered carbon dioxide is recycled within the process.

In some embodiments, at least some of the recovered carbon dioxide is sequestered into a geological formation. Exemplary geological formations include underground caverns or geological storage horizons, where the $CO_2$ gas can be permanently stored. In some embodiments, underground caverns or geological storage horizons are contained in active or abandoned oil or natural gas fields. In certain embodiments, the $CO_2$ gas is injected unto an active oil or natural gas field and serves to increase production of oil or natural gas, where the $CO_2$ gas substantially remains sequestered in that oil or natural gas field during and after production.

In addition to the methane-containing biogas as a primary product, there are a large number of potential co-products that may be isolated within the process, in variations.

Figure 11:
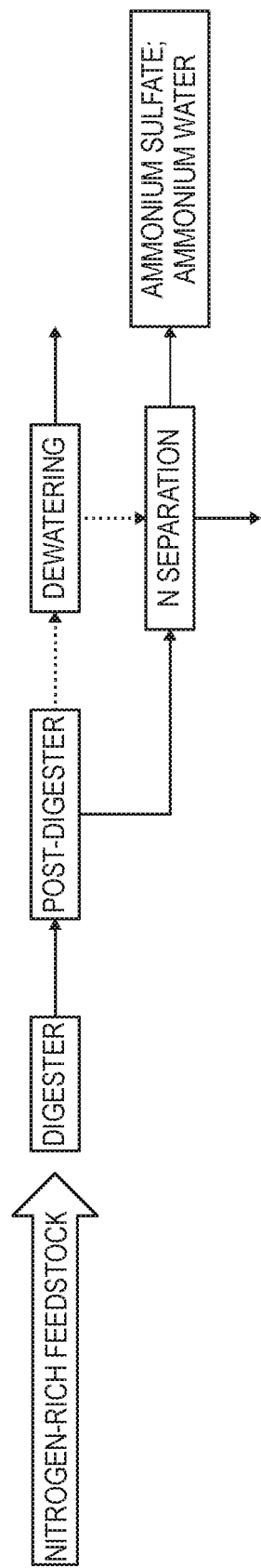
FIG. 11 depicts some process and system embodiments in which the starting feedstock (fed to the digester) is rich in nitrogen, and nitrogen-containing compounds are recovered from the digester slurry or from a liquid digestate derived therefrom and the remaining low-nitrogen liquid may be wholly or partially reused in the digestion process for dilution purposes.

In some embodiments, the process further comprises recovery of a nitrogen-containing compound directly from the digester slurry, without necessarily first separating the digester slurry into a solid phase and a liquid phase (see FIG. 11). The nitrogen-containing compound may be, for example, ammonium sulfate (($NH_4$)$_2SO_4$), ammonium water (also known as ammonium hydroxide, $NH_4OH$), or a combination thereof.

The nitrogen-containing compound(s) are recovered by separation, in the embodiment of FIG. 11. The nitrogen-containing compound(s) may be recovered via stripping the digester slurry with a stripping gas such as $N_2$ and/$CO_2$. Stripping may be done using air or steam as a stripping gas, for example. In some embodiments, nitrogen separation is accomplished by imposing a negative pressure (preferably 0.4 bar or lower) on the liquid while heating the liquid to preferably to about 65-75° C., thus causing $CO_2$ and $NH_3$ gas separation out from the liquid. The gaseous $CO_2$/$NH_3$ stream may be then subjected to reaction in a separate vessel with sulfuric acid or with water and gypsum, to form ammonia sulfate and calcium carbonate, which are both valuable fertilizers. Note that in FIG. 11, the digester slurry may be fed directly to dewatering and/or to the nitrogen (N) separation step, without first conveying to a post-digester.

In preferred embodiments, the process further comprises separating the digester slurry into a liquid digestate and a solid digestate. This solid/liquid separation may be referred to as "dewatering" and may employ known apparatus, such as (but not limited to) screw presses, drum filters, sieves, decanters, and centrifuges, any of which may be gravity fed or fed using a pump, for example. A polymer may be used to aggregate the fine solids together, in some embodiments. In principle, solid/liquid separation may be done by evaporating the liquid phase into a vapor phase, leaving the solid phase behind, and separately condensing the vapor phase back into a liquid. The solid/liquid separation may be done as a single step or in a multiple-step configuration, and is preferably operated continuously. To achieve a high solids capture rate without using flocculants or polymer chemicals, a multi-step mechanical separation process is preferred. A first step may involve a sieve drum or screw press dewatering step, capturing the coarse fibers and solids, followed by a decanter or filter step to capture the fine solids.

Generally, the liquid digestate may be recovered as a co-product selected from the group consisting of a fuel, biochar, pyrolysis oil, soil conditioner, agricultural fertilizer, organic soil product, soil enhancement material, landfill conditioner, and combinations thereof. The liquid digestate may be recovered as a nitrogen-containing compound (e.g., ($NH_4$)$_2SO_4$ or $NH_4OH$).

In some embodiments, the liquid digestate is recovered as a co-product that is a fine-particles slurry containing from about 1 wt % to about 10 wt % total solids, from about 0.2 wt % to about 4 wt % nitrogen (elemental N basis), from about 0.05 wt % to about 2 wt % phosphorous (element P basis), and from about 0.1 wt % to about 2 wt % potassium (element K basis), with the balance being water. A "fine-particles slurry" is a solid/liquid slurry within which fine particles do not normally settle out of the slurry. Optionally, the fine-particles slurry is dried to remove most or all water, generating a fine-particles solid material.

Optionally, some or all of the liquid digestate may be recycled within the process. For example, the liquid digestate may be recycled to step (b) and/or step (c). In certain embodiments, the liquid digestate is utilized to directly generate steam that steam-extracts or steam-explodes the size-reduced lignocellulosic material and/or the lignocellulosic pellets or extrudates. In these or other embodiments, liquid digestate is recycled to step (d), wherein the liquid digestate has a ratio of carbon to nitrogen, on an elemental weight basis, of about 30 or less, about 20 or less, or about 10 or less.

The liquid digestate may be combusted to provide digestate energy, which may be utilized elsewhere within the process, such as for process heating or for mechanical energy input. Typically, at least some water is removed from the liquid digestate prior to combustion, or the liquid digestate is combined with another process material (e.g., lignin) that has good combustion potential, for better thermal efficiency. Combustion may be carried out using well-known combustion or incineration methods and apparatus.

The solid digestate may also be recovered as a co-product, whether or not the liquid digestate is recovered as a co-product. In various embodiments, the solid digestate is recovered as a co-product selected from the group consisting of a solid fuel, biochar, pyrolysis oil, soil conditioner, agricultural fertilizer, organic soil product, soil enhancement material, landfill conditioner, and combinations thereof.

In some embodiments, the solid digestate is recovered as a co-product that is a fibrous humid cake containing from about 10 wt % to about 50 wt % total solids, from about 0.1 wt % to about 2 wt % nitrogen (elemental N basis), from about 0.1 wt % to about 3 wt % phosphorous (element P basis), and from about 0.05 wt % to about 1 wt % potassium (element K basis), with the balance being primarily water. A "fibrous humid cake" is a wet solid material formed from agglomerated solid digestate fibers. Optionally, the fibrous humid cake is dried to remove most or all water, generating a fibrous dry cake.

Optionally, some or all of the solid digestate may be recycled within the process. For example, solid digestate may be recycled back to one or more anaerobic digesters, or to a post-digester (when present), or to a hydrolysis unit (when present).

In some embodiments, solid digestate is combusted to provide digestate energy, which may be utilized elsewhere within the process, such as for process heating or for mechanical energy input. Combustion of solid digestate may be carried out using well-known combustion or incineration methods and apparatus.

In some embodiments, solid digestate is gasified to generate syngas (a mixture of $H_2$ and CO). Syngas may be generated from solid digestate via steam reforming, oxidative gasification, or other known gasification technologies. See, for example, Molino et al., "Biomass gasification technology: The state of the art overview", Journal of Energy Chemistry, Volume 25, Issue 1, Pages 10-25 (January 2016), which is hereby incorporated by reference herein.

The syngas may be introduced to one or more anaerobic digesters, to one or more hydrolysis units within the process, and/or to one or more post-digesters within the process. In related embodiments, the syngas is first separated into $H_2$ and CO, or into $H_2$-enriched syngas. The $H_2$ or $H_2$-enriched syngas may then be introduced to one or more anaerobic digesters, to one or more hydrolysis units within the process, and/or to one or more post-digesters within the process. The digester, post-digester, and/or hydrolysis unit is operated at effective hydrogenotrophic fermentation conditions to generate additional methane-containing biogas from the $H_2$ or $H_2$-enriched syngas.

In some embodiments (e.g., FIG. 9), solid digestate is pyrolyzed to generate a pyrolysis solid phase, a pyrolysis liquid phase, and a pyrolysis gas phase. The pyrolysis liquid phase may be characterized as pyrolysis oil or bio-oil, and may be recovered as a co-product or combusted to produce energy, for example. The pyrolysis gas phase may be recovered as a co-product or combusted to produce energy, for example. The pyrolysis solid phase may be recovered as a co-product or combusted to produce energy, for example.

Optionally, a portion of the pyrolysis solid phase is recycled to one or more anaerobic digesters and/or to a post-digester disposed downstream of the anaerobic digesters. The pyrolysis solid phase may act as an activated carbon to adsorb impurities within an anaerobic digester or post-digester, thereby enhancing biogas yield, for example.

Another potential co-product from the process is lignin, when the starting lignocellulosic feedstock contains lignin. Lignin or a lignin-rich material may be recovered directly from the digester slurry, from the liquid digestate, and/or from the solid digestate. Recovery of lignin from digester slurry, liquid digestate, or solid digestate may be accomplished using an organic acid such as sulfuric acid, phosphoric acid, or acetic acid, or an alcohol such as ethanol, to dissolve the biomass, followed by a precipitation step using an ether (e.g., isopropyl ether) to precipitate the cellulose and hemicellulose, separating cellulose and hemicellulose from the mixture and feeding it into the digestion line, while separating the lignin from the liquid stream coming from the cellulose/hemicellulose separation, optionally followed by lignin fractioning with enzymes, for example. Lignin has a wide variety of known uses, including combustion to generate energy, gasification to generate syngas, recovery as a solid fuel or a liquid fuel, or recovery as a biopolymer for use in polymer composites, for example.

As will be appreciated by a person skilled in the biorefinery art, many process variations are possible, including but not limited to the embodiments depicted in FIGS. 1-20 (described later) and other embodiments that utilize the principles taught herein. It is also noted that the overall process, and any sub-steps within the process, may be conducted continuously, semi-continuously, or as a batch process, in various embodiments.

Some variations provide a process for converting a lignocellulosic feedstock into methane, the process comprising:

(a) grinding or milling a lignocellulosic feedstock, to generate a size-reduced lignocellulosic material;

(b) pelletizing the size-reduced lignocellulosic material, to generate a plurality of lignocellulosic pellets;

(c) feeding the lignocellulosic pellets, or a slurry formed therefrom, into one or more anaerobic digesters operated at effective fermentation conditions to generate methane-containing biogas and a digester slurry; and (d) recovering the methane-containing biogas from the one or more anaerobic digesters.

Note that in these variations, a pretreatment chemical is not necessarily added.

Some variations provide a process for converting a lignocellulosic feedstock into methane, the process comprising:

(a) grinding or milling a lignocellulosic feedstock, to generate a size-reduced lignocellulosic material;

(b) introducing a pretreatment chemical to the size-reduced lignocellulosic material;

(c) steam-exploding the size-reduced lignocellulosic material, to generate pretreated lignocellulosic material;

(d) feeding the pretreated lignocellulosic material into one or more anaerobic digesters operated at effective fermentation conditions to generate methane-containing biogas and a digester slurry, wherein the anaerobic digesters each contain thermophilic bacteria, and wherein the effective fermentation conditions include a temperature from about 50° C. to about 60° C., a pH from about 7 to about 8, a residence time from about 10 days to about 60 days, total suspended solids from about 1 wt % to about 40 wt %, and organic dry matter content from about 30 wt % to about 90 wt % of total suspended solids; and (e) recovering the methane-containing biogas from the one or more anaerobic digesters.

In these variations, step (b) may be conducted prior to step (c), or vice-versa. Optionally, step (b) and step (c) are conducted simultaneously, i.e. the pretreatment chemical is added to the size-reduced lignocellulosic material during the step of steam explosion.

Some variations provide a process for converting a lignocellulosic feedstock into methane, the process comprising:

(a) grinding or milling a lignocellulosic feedstock, to generate a size-reduced lignocellulosic material comprising cellulose and lignin;

(b) introducing a solvent for biomass to the size-reduced lignocellulosic material, thereby generating dissolved lignocellulosic material;

(c) introducing a cellulose precipitant to the dissolved lignocellulosic material, thereby generating (i) a cellulose-rich stream containing precipitated cellulose and (ii) a first intermediate stream comprising the lignin, the solvent for biomass, and the cellulose precipitant;

(d) introducing a lignin precipitant to the intermediate stream, thereby generating (i) a lignin-rich stream containing precipitated lignin and (ii) a second intermediate stream comprising the solvent for biomass, the cellulose precipitant, and the lignin precipitant;

(e) recovering and recycling the solvent for biomass, the cellulose precipitant, and the lignin precipitant from the second intermediate stream;

(f) feeding the cellulose-rich stream into one or more anaerobic digesters operated at effective fermentation conditions to generate methane-containing biogas and a digester slurry; and (g) recovering the methane-containing biogas from the one or more anaerobic digesters.

In some embodiments, the solvent for biomass is selected from acids and alcohols, such as from the group consisting of acetic acid, phosphoric acid, sulfuric acid, ethanol, and combinations thereof.

In some embodiments, the cellulose precipitant (agent to cause precipitation of cellulose) is selected from ethers, such as isopropyl ether. The cellulose precipitant, in some embodiments, also causes precipitation of hemicellulose. Thus when the size-reduced lignocellulosic material further comprises hemicellulose, the cellulose-rich stream may contain precipitated hemicellulose as well.

In some embodiments, the lignin precipitant (agent to cause precipitation of lignin) is selected from ethers, such as isopropyl ether. The lignin precipitant may be the same as the cellulose precipitant. The lignin precipitant, in some embodiments, also causes precipitation of hemicellulose. Thus when the size-reduced lignocellulosic material further comprises hemicellulose, the lignin-rich stream may contain precipitated hemicellulose as well.

In certain embodiments, hemicellulose is recovered from the first intermediate stream and/or the second intermediate stream and introduced to the one or more anaerobic digesters.

In some embodiments, step (e) includes addition of wash water followed by evaporation. In these or other embodiments, step (e) includes dewatering in a screw press and/or centrifuge.

The process may further include adding enzymes to the lignin-rich stream to fractionate lignin by molecular weight, thereby generating a plurality of lignin-rich streams with different average lignin molecular weights. Suitable enzymes are MetZyme® LIGNO™ enzymes (MetGen Oy, Kaarina, Finland).

In some embodiments, the process further comprises recovering the lignin-rich stream. For example, at least a portion of the lignin-rich stream may be combusted to provide energy for the process. At least a portion of the lignin-rich stream may be gasified to provide syngas. At least a portion of the lignin-rich stream may be pyrolyzed to generate a pyrolysis solid phase, a pyrolysis liquid phase, and a pyrolysis gas phase.

When a pyrolysis solid phase is produced from lignin (or other material), the process may include feeding the pyrolysis solid phase to one or more anaerobic digesters and/or to a post-digester disposed downstream of the anaerobic digesters. In certain embodiments, the digester slurry, a solid portion thereof, and/or a liquid portion thereof is co-pyrolyzed with the lignin-rich stream.

Some variations provide a process for converting a lignocellulosic feedstock into methane, the process comprising:

(a) grinding or milling a lignocellulosic feedstock, to generate a size-reduced lignocellulosic material;

(b) introducing a pretreatment chemical to the size-reduced lignocellulosic material;

(c) pelletizing or extruding the size-reduced lignocellulosic material, to generate a plurality of lignocellulosic pellets or extrudates;

(d) feeding the lignocellulosic pellets or extrudates, or a slurry formed therefrom, into one or more anaerobic digesters operated at effective fermentation conditions to generate methane-containing biogas and a digester slurry;

(e) separating the methane-containing biogas into methane-rich gas and $CO_2$-rich gas;

(f) recovering the methane-rich gas; and (g) recovering or recycling the $CO_2$-rich gas comprising carbon dioxide.

In some embodiments, at least some of the $CO_2$-rich gas is sequestered into a geological formation.

In some embodiments, at least some of the $CO_2$-rich gas is recycled to the one or more anaerobic digesters, wherein hydrogen is introduced to the one or more anaerobic digesters, and wherein the hydrogen and the carbon dioxide react hydrogenotrophically to generate additional methane.

In these or other embodiments, at least some of the $CO_2$-rich gas is recycled to a hydrolysis unit disposed upstream of the one or more anaerobic digesters, wherein hydrogen is introduced to the hydrolysis unit, and wherein the hydrogen and the carbon dioxide react hydrogenotrophically to generate additional methane.

In these or other embodiments, at least some of the $CO_2$-rich gas is recycled to a post-digester disposed downstream of the one or more anaerobic digesters, wherein hydrogen is introduced to the post-digester, and wherein the hydrogen and the carbon dioxide are converted by hydrogenotrophic bacteria (e.g., *Methanobacterium* species, Methanomicrobiales species, Methanobacteriales species, or *Methanothermobacter thermautotrophicus*) to generate additional methane In some embodiments, at least some of the $CO_2$-rich gas is introduced to a catalytic methane-generation reactor, wherein hydrogen is introduced to the catalytic methane-generation reactor, and wherein the wherein the hydrogen and the carbon dioxide react catalytically to generate additional methane, such as via the Sabatier reaction that converts $CO_2$ and $H_2$ into $CH_4$ and $H_2O$ at high temperatures, such as from about 250° C. to about 500° C. Chemical catalysts for generating methane from $CO_2$ and $H_2$ include, but are not limited to, nickel and ruthenium. Catalysts are optionally disposed on a catalyst support, such as alumina.

Some variations provide a process for converting a lignocellulosic feedstock into methane, the process comprising:

(a) grinding or milling a lignocellulosic feedstock, to generate a size-reduced lignocellulosic material;

(b) introducing a pretreatment chemical to the size-reduced lignocellulosic material;

(c) pelletizing or extruding the size-reduced lignocellulosic material, to generate a plurality of lignocellulosic pellets or extrudates;

(d) feeding the lignocellulosic pellets or extrudates, or a slurry formed therefrom, into a first anaerobic digester operated at effective acetoclastic fermentation conditions to generate methane-containing biogas and an intermediate digester slurry;

(e) feeding the intermediate digester slurry, hydrogen, and carbon dioxide into a second anaerobic digester operated at effective hydrogenotrophic fermentation conditions to generate additional methane-containing biogas and a digester slurry; and (f) recovering the methane-containing biogas and the additional methane-containing biogas from the first and second anaerobic digesters.

In any of the above embodiments utilizing hydrogen, any source of hydrogen may be used. Hydrogen may be derived from a biological hydrolysis step carried out in a hydrolysis unit disposed upstream of the first anaerobic digester. At least some of the hydrogen may be generated within the first anaerobic digester. In some embodiments, hydrogen is provided from water electrolysis. In some embodiments, hydrogen is provided from syngas generated from a carbon-containing intermediate material (e.g., solid digestate or lignin) recovered from the process. In the case of first and second anaerobic digesters, solid digestate may be recovered from the intermediate digester slurry and/or from the digester slurry that exits from the second anaerobic digester.

The carbon dioxide for step (e) may be derived from a biological hydrolysis step carried out in a hydrolysis unit disposed upstream of the first anaerobic digester. The carbon dioxide may be generated from a solid digestate recovered from the intermediate digester slurry and/or from the digester slurry, such as via combustion. Also, carbon dioxide recovered from a biogas upgrader may be used in step (e).

In some embodiments, in step (e), the hydrogen and the carbon dioxide are present at a $H_2/CO_2$ volumetric ratio of about 2 to about 6, such as about 3 to about 5, or about 3.5 to about 4.5, and preferably about 4.0.

In some embodiments, the methane-containing biogas is conveyed to the second anaerobic digester, wherein both of the methane-containing biogas and the additional methane-containing biogas are recovered from the second anaerobic digester. Optionally, heat may be recovered from the second anaerobic digester, wherein the heat may be used in the first anaerobic digester or for other process heating needs.

Some embodiments provide a process for converting a lignocellulosic feedstock into methane, the process comprising:

(a) providing a lignocellulosic feedstock comprising grass straw and wheat straw;

(b) grinding or milling the lignocellulosic feedstock, to generate a size-reduced lignocellulosic material;

(c) introducing potassium hydroxide to the size-reduced lignocellulosic material, thereby generating conditioned lignocellulosic material;

(d) cubing the conditioned lignocellulosic material, to generate a plurality of lignocellulosic cubes;

(e) conveying the lignocellulosic cubes from a first location to a second location within the process;

(f) forming a lignocellulosic slurry from (i) the lignocellulosic cubes and (ii) a liquid stream comprising water;

(g) feeding the lignocellulosic slurry into a plurality of anaerobic digesters each operated at effective fermentation conditions to generate methane-containing biogas and a digester slurry, wherein the anaerobic digesters each contain thermophilic bacteria, and wherein the effective fermentation conditions include a temperature from 50° C. to 60° C., a pH from 7.2 to 7.9, a residence time from 15 days to 60 days, total suspended solids from 5 wt % to 20 wt %, and organic dry matter content from 60 wt % to 75 wt % of total dry matter;

(h) recovering the methane-containing biogas, directly or indirectly, from the one or more anaerobic digesters;

(i) separating the digester slurry into a liquid digestate and a solid digestate;

(j) recycling at least some of the liquid digestate back to step (d), step (f), and/or step (g); and (k) optionally composting at least some of the solid digestate.

Some embodiments provide a process for converting a lignocellulosic feedstock into methane, the process comprising:

(a) providing a lignocellulosic feedstock comprising grass straw and wheat straw;

(b) grinding or milling the lignocellulosic feedstock, to generate a size-reduced lignocellulosic material;

(c) introducing potassium hydroxide to the size-reduced lignocellulosic material, thereby generating conditioned lignocellulosic material;

(d) extruding the conditioned lignocellulosic material, to generate a plurality of lignocellulosic extrudates;

(e) conveying the lignocellulosic extrudates from a first location to a second location within the process;

(f) forming a lignocellulosic slurry from (i) the lignocellulosic extrudates and (ii) a liquid stream comprising water;

(g) feeding the lignocellulosic slurry into a plurality of anaerobic digesters each operated at effective fermentation conditions to generate methane-containing biogas and a digester slurry, wherein the anaerobic digesters each contain thermophilic bacteria, and wherein the effective fermentation conditions include a temperature from 50° C. to 60° C., a pH from 7.2 to 7.9, a residence time from 15 days to 60 days, total suspended solids from 5 wt % to 20 wt %, and organic dry matter content from 60 wt % to 75 wt % of total dry matter;

(h) recovering the methane-containing biogas, directly or indirectly, from the one or more anaerobic digesters;

(i) separating the digester slurry into a liquid digestate and a solid digestate;

(j) recycling at least some of the liquid digestate back to step (d), step (f), and/or step (g); and (k) optionally composting at least some of the solid digestate.

Variations of the present disclosure also provide systems, i.e. a plurality of physical apparatus configured to carry out a process. Generally, commercially available equipment known to those skilled in the art of biorefining and chemical engineering may be utilized in specific system and process arrangements, as described herein.

In some variations, a system is provided for converting a lignocellulosic feedstock into methane, the system comprising:

(a) a grinding or milling unit configured for grinding or milling a lignocellulosic feedstock, to generate a size-reduced lignocellulosic material;

(b) a pelletizer or extruder configured for pelletizing or extruding the size-reduced lignocellulosic material, to generate a plurality of lignocellulosic pellets or extrudates;

(c) one or more anaerobic digesters configured to (i) receive the lignocellulosic pellets or extrudates, or a slurry formed therefrom, and to (ii) generate methane-containing biogas and a digester slurry;

(d) a recovery system configured to capture the methane-containing biogas from the one or more anaerobic digesters; and (e) optionally a solid/liquid separation unit configured to separate the digester slurry into a solid digestate and a liquid digestate, wherein the solid/liquid separation unit has a first outlet for the solid digestate and a second outlet for the liquid digestate.

In some variations, a system is provided for converting a lignocellulosic feedstock into methane, the system comprising:

(a) a grinding or milling unit configured for grinding or milling a lignocellulosic feedstock, to generate a size-reduced lignocellulosic material;

(b) a steam-explosion apparatus configured for steam-exploding the size-reduced lignocellulosic material, to generate pretreated lignocellulosic material;

(c) one or more anaerobic digesters configured to (i) receive the pretreated lignocellulosic material and to (ii) generate methane-containing biogas and a digester slurry;

(d) a recovery system configured to capture the methane-containing biogas from the one or more anaerobic digesters; and (e) optionally a solid/liquid separation unit configured to separate the digester slurry into a solid digestate and a liquid digestate, wherein the solid/liquid separation unit has a first outlet for the solid digestate and a second outlet for the liquid digestate.

In some variations, a system is provided for converting a lignocellulosic feedstock into methane, the system comprising:

(a) a grinding or milling unit configured for grinding or milling a lignocellulosic feedstock, to generate a size-reduced lignocellulosic material;

(b) a biomass-dissolution unit configured for generating dissolved lignocellulosic material;

(c) a cellulose-precipitation unit configured for generating a cellulose-rich stream containing precipitated cellulose;

(d) a lignin-precipitation unit configured for generating a lignin-rich stream containing precipitated lignin;

(e) one or more anaerobic digesters configured to (i) receive the cellulose-rich stream and to (ii) generate methane-containing biogas and a digester slurry; and (f) a recovery system configured to capture the methane-containing biogas from the one or more anaerobic digesters.

In some variations, a system is provided for converting a lignocellulosic feedstock into methane, the system comprising:

(a) a grinding or milling unit configured for grinding or milling a lignocellulosic feedstock, to generate a size-reduced lignocellulosic material;

(b) a pelletizer or extruder configured for pelletizing or extruding the size-reduced lignocellulosic material, to generate a plurality of lignocellulosic pellets or extrudates;

(c) one or more anaerobic digesters configured to (i) receive the lignocellulosic pellets or extrudates, or a slurry formed therefrom, and to (ii) generate methane-containing biogas and a digester slurry;

(d) a recovery system configured to capture the methane-containing biogas from the one or more anaerobic digesters, wherein the methane-containing biogas contains $CO_2$; and (e) a biogas upgrading unit configured for separating the methane-containing biogas into methane-rich gas and $CO_2$-rich gas.

In some variations, a system is provided for converting a lignocellulosic feedstock into methane, the system comprising:

(a) a grinding or milling unit configured for grinding or milling a lignocellulosic feedstock, to generate a size-reduced lignocellulosic material;

(b) a pelletizer or extruder configured for pelletizing or extruding the size-reduced lignocellulosic material, to generate a plurality of lignocellulosic pellets or extrudates;

(c) a first anaerobic digester configured to (i) receive the lignocellulosic pellets or extrudates, or a slurry formed therefrom, and to (ii) generate methane-containing biogas and an intermediate digester slurry;

(d) a second anaerobic digester configured to (i) receive the intermediate digester slurry, hydrogen, and carbon dioxide and to (ii) generate additional methane-containing biogas and a digester slurry; and (e) a recovery system configured to capture the methane-containing biogas and the additional methane-containing biogas.

Variations of the present disclosure provide one or more products produced by a process comprising one or more process configurations as disclosed in this specification, including the drawings. Such products include, but are not limited to, biogas, fibrous humid cake, fine-particles slurry, lignin, biochar, energy (as heat and/or electricity), fertilizers, soil conditioners, land conditioners, ammonium sulfate, ammonium hydroxide, and sequestered $CO_2$.

Exemplary Embodiments

The following non-limiting description makes reference to the accompanying drawings (FIGS. 1-20), as well as designations (on those drawings) of various process and system embodiments and options. Note that dotted or dashed lines explicitly denote optional streams and unit operations. Furthermore, in any of these drawings, one or more steps, unit operations, or streams may optionally be omitted, without departing from the spirit and principles of the present disclosure. As an example, various purge streams may be included at various points in the process, in order to avoid the build-up of certain components being recycled. Likewise, one or more steps, unit operations, or streams may optionally be added, without departing from the spirit and principles of the present disclosure. Any unit operation may be duplicated via parallel process lines (e.g., multiple digester lines) to accommodate a desired process capacity. Also, various tanks (e.g., storage tanks, buffer tanks, mix tanks, etc.), pumps, conveyers, and minor streams (e.g., nutrient inputs) may be included in any embodiments and are not shown in the drawings for purposes of clarity.

Referring to FIG. 1, an anaerobic digestion process is provided, in which incoming feedstock is converted to biogas, fibrous humid cake, and a fine-particles slurry. The feedstock may be selected from lignocellulosic feedstocks, waste feedstocks, or a combination thereof. For example, lignocellulosic feedstocks may be selected from grass straw, corn stover, wheat straw, rice straw, cotton burr, other agricultural residues, or a combination thereof. Waste feedstocks may be selected from food waste, agricultural organic waste, industrial organic waste, livestock manure, or a combination thereof, for example. In various embodiments, the weight ratio of lignocellulosic feedstock to waste feedstock is selected from about 0.3:1 to about 3:1. Different feedstocks may be mixed in a ratio between lignocellulosic feedstock and waste feedstock such that the majority of the liquid digestate after solid-liquid separation (from unit "Dewatering #2") is recycled and little or no liquid digestate is disposed of or transported offsite, via the optional water purge shown in FIG. 1.

In addition to lignocellulosic feedstocks and/or waste feedstocks, other components may be present in the feedstock stream, such as nitrogen-rich components (e.g., nitrogen-rich liquid digestate). In some embodiments, different feedstocks including a nitrogen-rich liquid digestate are mixed to achieve a beneficial C:N ratio in the feed. A beneficial C:N ratio (by elemental mass) is preferably at most 30:1, more preferably at most 20:1, and most preferably at most 10:1 (i.e., more nitrogen-rich), in the feedstock mixture.

In the process of FIG. 1, mechanical pretreatment of lignocellulosic feedstock (or other feedstocks) is carried out via grinding or milling. The ground or milled feedstock is subsequently subjected to pelletizing, extruding, or a combination thereof. Various chemicals may be added to improve the disintegration of the lignocellulosic structure of the feedstock. These chemicals may include, but are not limited to, potassium hydroxide (KOH), sodium hydroxide (NaOH), calcium hydroxide ($Ca(OH)_2$), calcium carbonate ($CaCO_3$), acetic acid, phosphoric acid, urea, aqueous ammonia, ammonium salts, and/or carbon dioxide to enhance the disintegration of the lignocellulosic structure of the feedstock. FIG. 1 shows the optional pretreatment chemicals added directly to the step of pelletizing or extruding, and it should be noted that in other embodiments, pretreatment chemicals are added before or after the step of pelletizing or extruding.

The pellets (e.g., cubes) or extrudates exiting the step of pelletizing or extruding may be fed directly to the digester. The pretreated lignocellulosic feedstock may be fed in form of pellets or extrudates into the digester by direct dry feed via conveyors or dry feed pumps, for example. Alternatively, or additionally, the pellets or extrudates may first be slurried in a liquid tank (not shown) upstream of the digester, and the wet slurry fed to the digester. In certain embodiments, the pretreated feedstock may be fed in form of pellets or extrudates into digester by adding liquid into a screw-fed pump and creating a pumpable mixture of pellets or extrudates and pumping this mixture to the digestion process. Pretreated lignocellulosic feedstock may be fed in the form of loose pretreated fibrous feedstock into screw-fed pumps, adding liquid into such pumps and creating a pumpable mixture for feeding to the digester.

Enzymes may be added to the primary digestion step (the digester of FIG. 1), to enhance the degradation rate of cellulose and hemicellulose contained in the lignocellulosic feedstock. Alternatively, or additionally, enzymes may be added to a post-digestion step, in the post-digester of FIG. 1, to enhance degradation of remaining lignocellulosic fibers.

In the process embodiment of FIG. 1, biogas is captured from both the digester as well as the post-digester. In some embodiments, biogas is not captured directly from the digester but rather is conveyed first to the post-digester, where the biogas is captured and recovered. In this disclosure, this embodiment is referred to as indirect recovery of biogas from the digester.

It is also noted that in some embodiments, a first digester (primary digester) and a second digester in series (post-digester) collectively form a sub-system that may be referred to as a digester, from which biogas is recovered.

The digester slurry exiting the post-digester may be recovered as a co-product itself, or may be recycled within the process, such as back to the digester, to enhance process stability and overall degradation of feedstock. The digester slurry may be dewatered via solid-liquid separation to form a solid digestate (shown as fibrous humid cake in FIG. 1) and a liquid digestate (shown as fine-particles slurry in FIG. 1). Recycle of liquid digestate may result in the majority of digestate product being in the form of fibrous humid cake. Liquid digestate may be treated by membranes or by an evaporation process to concentrate minerals and nutrients. This option can create a favorable liquid, primarily free of suspended solids, for the dilution of lignocellulosic feedstock in the pretreatment process.

Some or all of the dewatered fibers or dried products may be burned to generate thermal energy for drying. Recovered fibers may be dried to create an enhanced product. In particular, for example, recovered fibers may be further dried and subsequently compressed, pelletized, blended with other materials, or a combination thereof.

Figure 2:
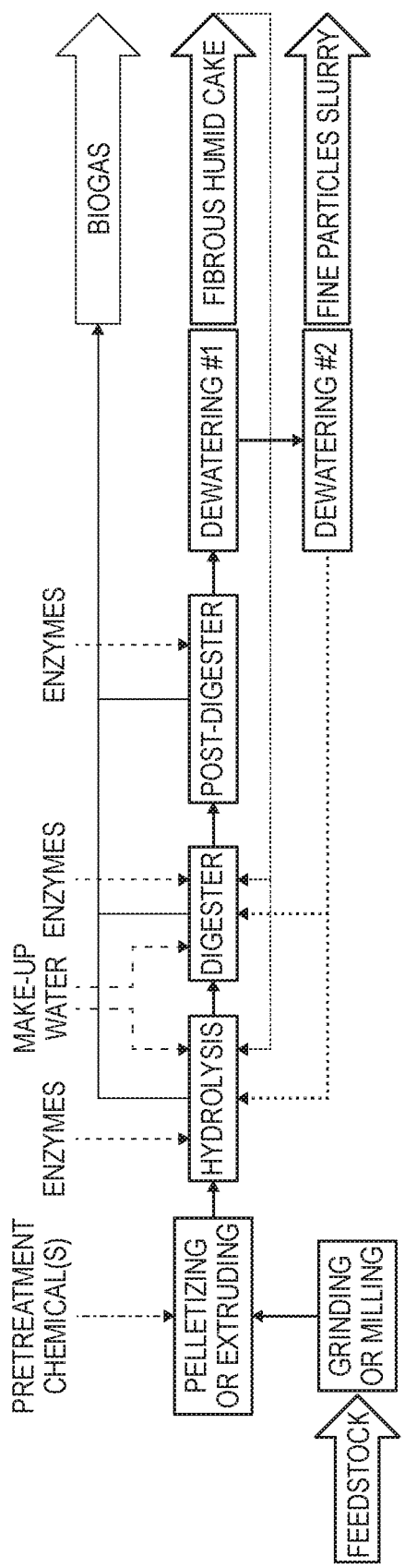
FIG. 2 depicts an exemplary anaerobic digestion process and system, in which incoming lignocellulosic feedstock is converted to biogas, fibrous humid cake, and a fine-particles slurry, with the inclusion of a hydrolysis unit upstream of the digester.

Referring to FIG. 2, an anaerobic digestion process is provided, in which incoming feedstock is converted to biogas, fibrous humid cake, and a fine-particles slurry. The embodiment of FIG. 2 is similar to FIG. 1, with the addition of a hydrolysis unit. The pretreated lignocellulosic feedstock may be fed in form of pellets or extrudates into the hydrolysis unit by direct dry feed via conveyors or dry feed pumps, for example.

The hydrolysis step in FIG. 2 is configured between mechanical pretreatment (with or without pretreatment chemicals) and digestion. Enzymes (e.g., cellulases) are introduced to the hydrolysis unit. Enzymes may be added in enzyme form, or in the form of living or dead microorganisms containing such enzymes.

The hydrolysis unit of FIG. 2 is preferably operated at or above the thermophilic temperature range to enhance the degradation of feedstock and the rate of this degradation. For example, the hydrolysis unit may be operated in a temperature range of about 50° C. to about 70° C. Optionally, small amounts of oxygen, air, or oxygen-enriched air may be added to the hydrolysis unit, for micro-aeration to enhance hydrolysis of biomass.

An off-gas of the hydrolysis unit may be conveyed into a biogas collection system to capture the released gases, such as hydrogen and carbon dioxide. FIG. 2 shows the hydrolysis off-gas being captured with the biogas generated in the digester and post-digester, but it should be understood that the hydrolysis off-gas may be separately recovered and processed.

Figure 3:
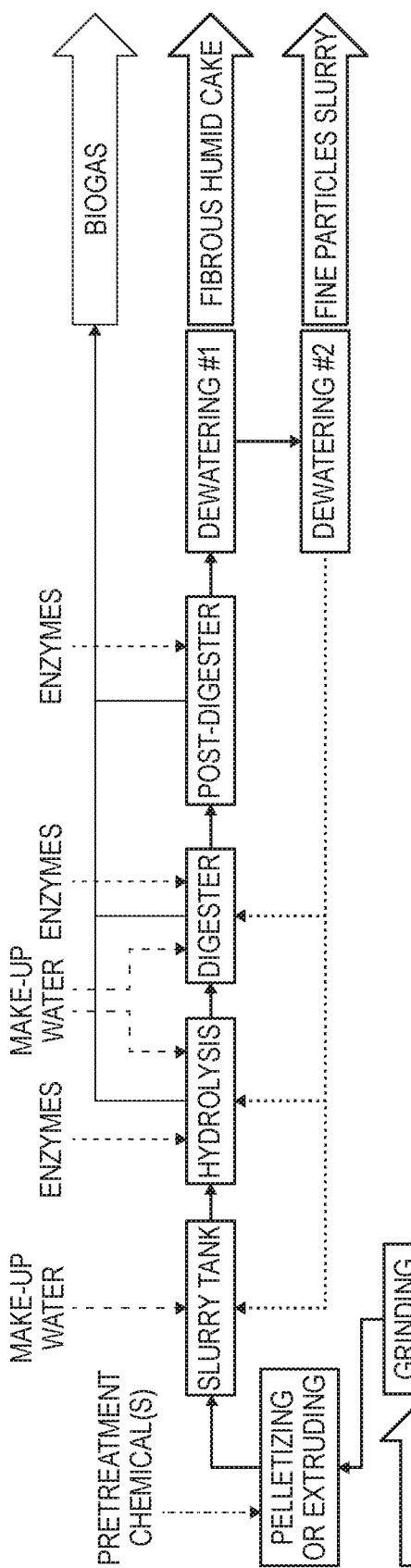
FIG. 3 depicts an exemplary anaerobic digestion process and system, in which incoming lignocellulosic feedstock is converted to biogas, fibrous humid cake, and a fine-particles slurry, with the inclusion of a hydrolysis unit upstream of the digester and a slurry tank for creating a wet feed to hydrolysis.

Referring to FIG. 3, an anaerobic digestion process is provided, in which incoming feedstock is converted to biogas, fibrous humid cake, and a fine-particles slurry. The embodiment of FIG. 3 is similar to FIG. 2, with the addition of a slurry tank for creating a wet feed from the pellets or extrudates.

Figure 4:
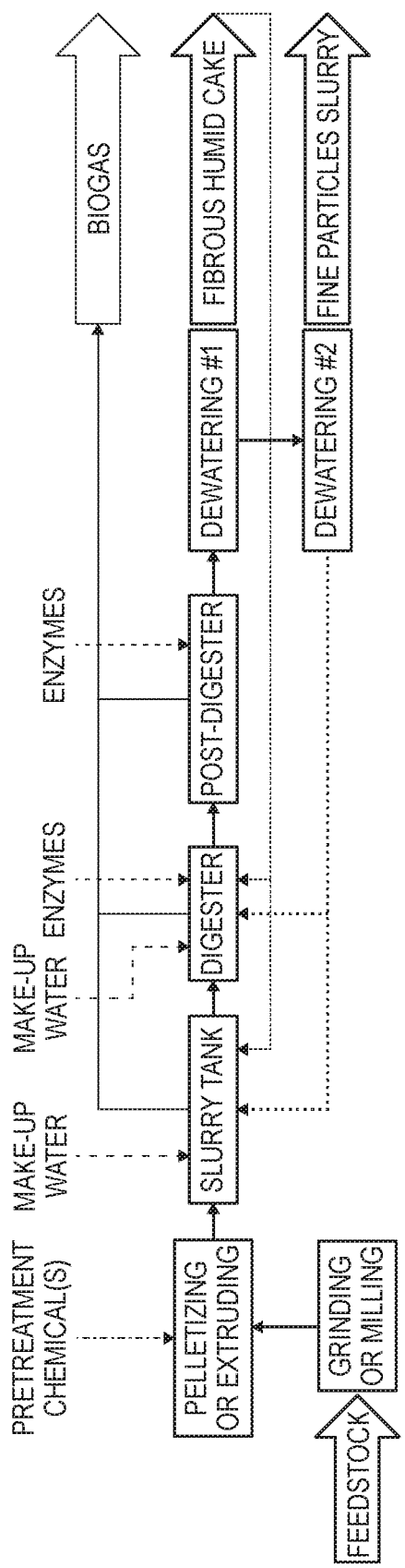
FIG. 4 depicts an exemplary anaerobic digestion process and system, in which incoming lignocellulosic feedstock is converted to biogas, fibrous humid cake, and a fine-particles slurry, with the inclusion of a slurry tank for creating a wet feed to the digester.

Referring to FIG. 4, an anaerobic digestion process is provided, in which incoming feedstock is converted to biogas, fibrous humid cake, and a fine-particles slurry. The embodiment of FIG. 4 is similar to FIG. 1, with the addition of a slurry tank for creating a wet feed from the pellets or extrudates.

Figure 5:
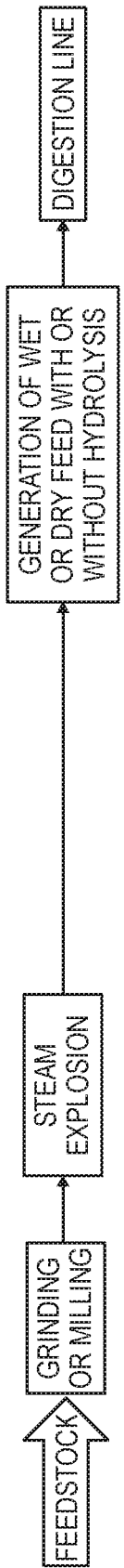
FIG. 5 depicts an exemplary anaerobic digestion process and system, in which incoming lignocellulosic feedstock is subjected to steam explosion instead of, or in addition to, pelletizing or extruding, to disintegrate the lignocellulosic feedstock.
Figure 6:
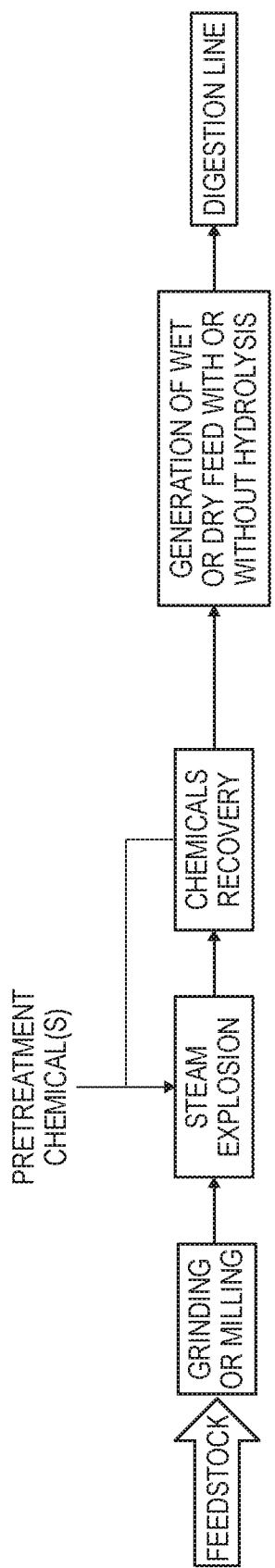
FIG. 6 depicts an exemplary anaerobic digestion process and system, in which incoming lignocellulosic feedstock is subjected to steam explosion with a pretreatment chemical, to disintegrate the lignocellulosic feedstock.

Referring to FIG. 5, in various embodiments a continuous or batchwise steam explosion process is employed instead of, or in addition to, pelletizing or extruding, to disintegrate the lignocellulosic feedstock. Optionally, one or more pretreatment chemicals (other than water) may be introduced into the steam explosion process to further enhance the disintegration of the lignocellulosic structure of feedstock, such as depicted in FIG. 6. An exemplary pretreatment chemical is sodium hydroxide. There is preferably a recovery step for the pretreatment chemicals after steam explosion, as shown in FIG. 6. The recovery of pretreatment chemicals may be done by evaporation, precipitation, ion exchange, membrane separation, centrifugation, or other means, depending on the pretreatment chemicals utilized.

Figure 7:
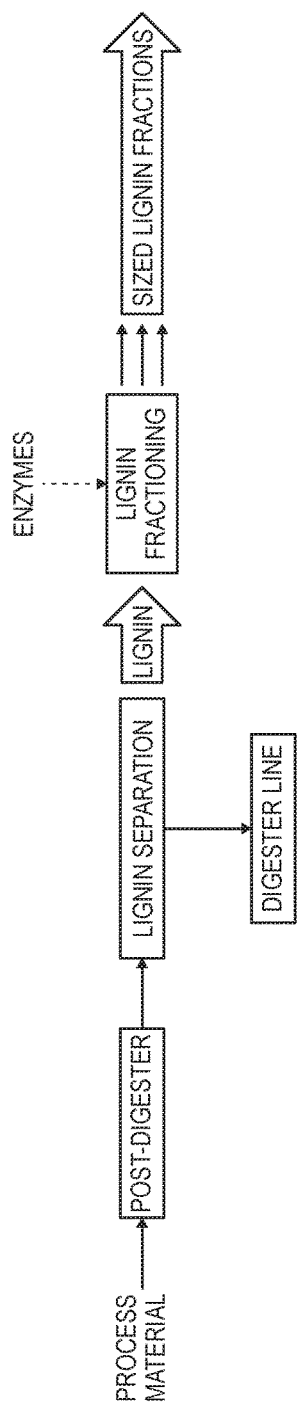
FIG. 7 depicts an exemplary lignin recovery process and system that may be applied to various process intermediate materials obtained from an anaerobic digestion process and system.

Referring to FIG. 7, a lignin recovery process may be applied to various process intermediate materials. The process intermediate material may be whole digester slurry, a liquid digestate, a solid digestate, a fine-solids sludge, or another stream containing lignin. Enzymes may be added to a step of lignin fractioning, to separate lignin according to size or molecular weight. Some or all of the dewatered fibers or dried products may be burned to generate the required thermal power for the drying process itself and/or for precipitant recovery (when lignin precipitants are utilized for lignin separation), which usually requires energy.

Figure 8:
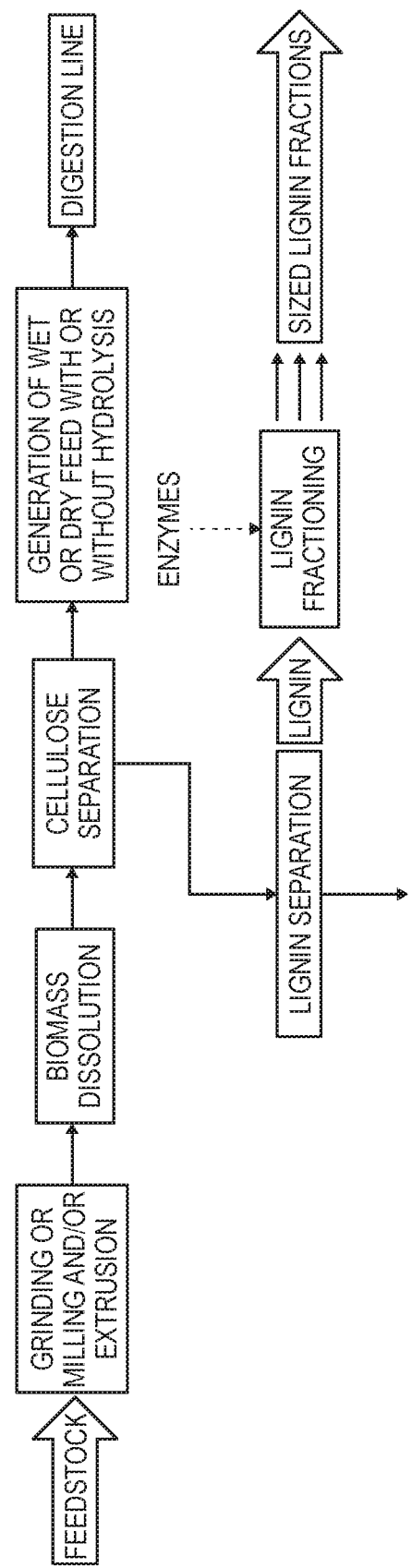
FIG. 8 depicts an exemplary anaerobic digestion process and system, in which incoming lignocellulosic feedstock is dissolved with a solvent to enhance disintegration of the feedstock, followed by separation of cellulose and potentially hemicellulose.

Referring to FIG. 8, a process step is added after mechanical pretreatment to introduce a solvent and moderate temperature to the feedstock to at least partially dissolve and/or suspend it and enhance the disintegration of the feedstock biomass. Optionally, a precipitant (precipitation agent) is added to the dissolved and/or suspended feedstock to precipitate predominantly cellulose and hemicellulose from the feedstock. The precipitant (when used) may be recovered and recycled. The cellulose-separation step creates an input (wet feed or dry feed) for digestion, and a liquid stream containing lignin. Cellulose separation may be accomplished with mechanical equipment such as screw presses or centrifuges. A precipitant may also be added to precipitate the lignin from the liquid stream. The precipitant for causing lignin precipitation may be the same or different than a precipitant that causes precipitation of cellulose, when a cellulose precipitant is used. Enzymes may be added to fractionate recovered lignin into various sizes of lignin for enhanced marketability. Wash water may be added before dewatering, to help recover solvent and, in some embodiments, precipitants, such as in a two-stage evaporation process.

Figure 9:
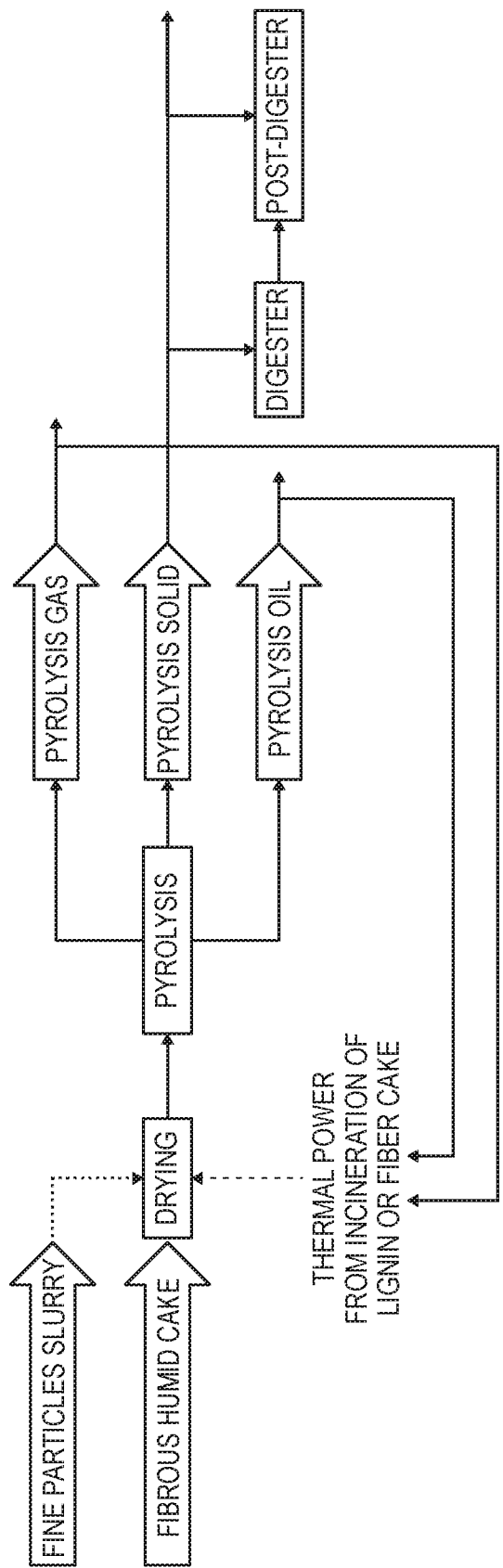
FIG. 9 depicts an exemplary anaerobic digestion process and system, in which solid digestate is pyrolyzed to generate pyrolysis gas, pyrolysis oil, and a pyrolysis solid phase that is whole or partially sent to the digester(s).

Referring to FIG. 9, in some embodiments solid digestate and optionally liquid digestate is dried and then pyrolyzed to generate a pyrolysis solid phase, a pyrolysis liquid phase, and a pyrolysis gas phase. The pyrolysis liquid phase may be characterized as pyrolysis oil or bio-oil, and may be recovered as a co-product or combusted to produce energy, for example. The pyrolysis gas phase also may be recovered as a co-product or combusted to produce energy, for example. The pyrolysis solid phase may be recovered as a co-product, combusted to produce energy, or some of it recycled within the process. Optionally, the pyrolysis solid phase is recycled to one or more anaerobic digesters and/or to a post-digester disposed downstream of the anaerobic digesters. Note that thermal energy for drying may be derived from incineration of pyrolysis gas and/or pyrolysis oil, lignin, fiber cake (e.g., solid digestate), or other carbon-containing materials derived from the process. Drying and pyrolysis may be combined into an integrated unit operation, in certain embodiments.

Figure 10:
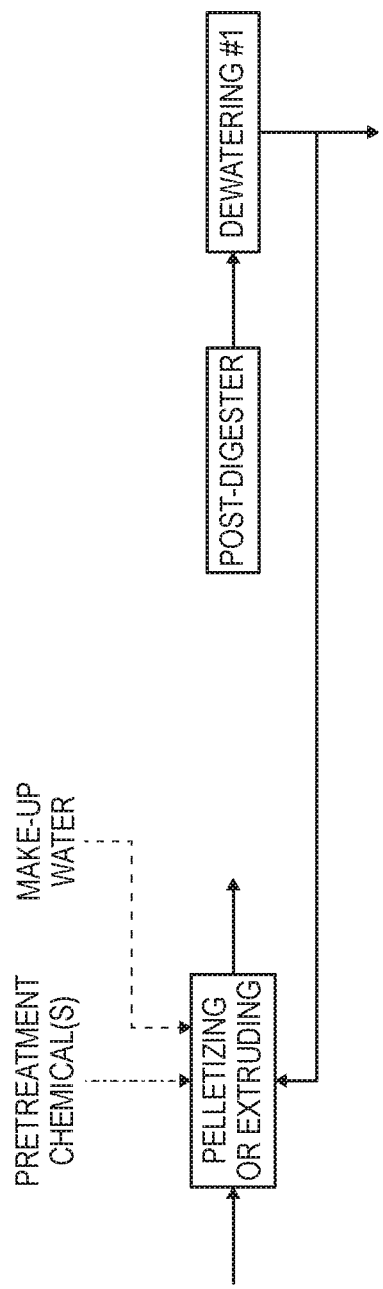
FIG. 10 depicts some process and system embodiments in which liquid digestate from dewatering is recycled to a pelletizing or extruding step, to create favorable humidity for steam explosion during mechanical treatment.

Referring to FIG. 10, in various embodiments liquid digestate (from dewatering #1 unit) is recycled to the pelletizing or extruding step, to create favorable humidity during mechanical treatment. This recycling can result in steam formation during the process and enhance the disintegration of lignocellulosic feedstock through known mechanisms, such as steam explosion or steam extraction. Make-up water may be added to the pelletizing or extruding step, depending on recycle rate and water concentration desired during pretreatment.

Referring to FIG. 11, when the starting feedstock (fed to the digester) is rich in nitrogen, nitrogen-containing compounds may be recovered from the digester slurry or from a liquid digestate derived therefrom. The recovery of nitrogen-containing compounds is accomplished in the unit denoted as "N separation" in FIG. 11, in which a nitrogen-containing compound may be recovered, such as (but not limited to) by stripping with a gas, membrane filtration, precipitation, or other means. Nitrogen-containing compounds include, but are not limited to, ammonium hydroxide (ammonia water) and ammonium sulfate.

Figure 12:
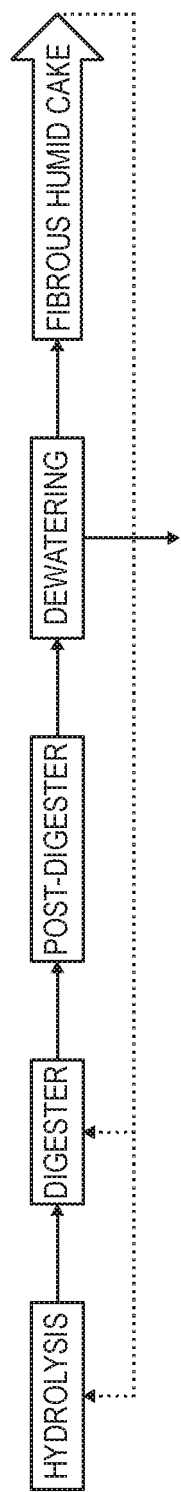
FIG. 12 depicts some process and system embodiments in which dewatered digestate fibers (fibrous humid cake) is recycled back into a hydrolysis unit and/or a digester.

Referring to FIG. 12, in various embodiments, dewatered digestate fibers (fibrous humid cake) may be recycled back into a hydrolysis unit and/or a digester. Recycling fibrous humid cake enhances the overall degradation rate of, and biogas productivity from, lignocellulosic fibers.

Figure 13:
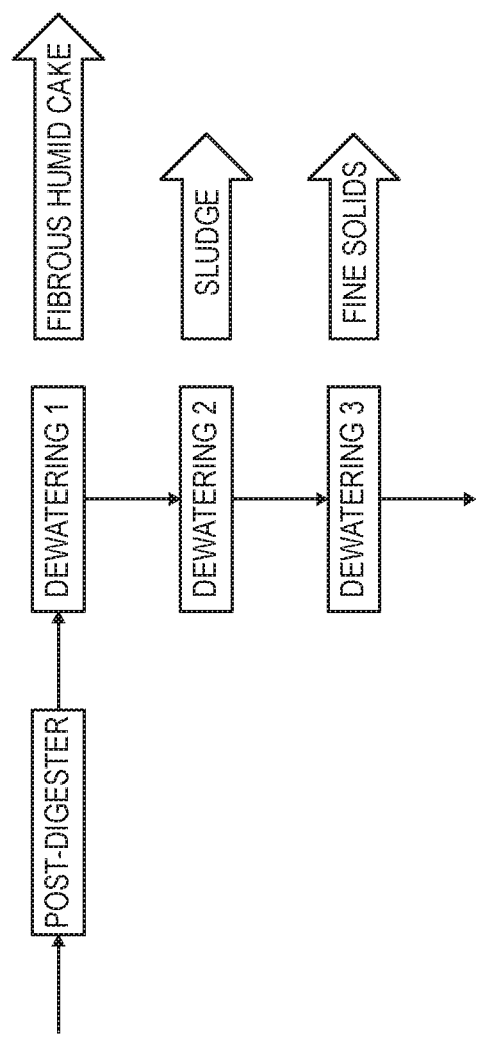
FIG. 13 depicts some process and system embodiments in which whole digestate (i.e., digester slurry) is mechanically dewatered in three dewatering steps, resulting in fibrous humid cake, sludge, and a fine-particles slurry, in some embodiments.

Referring to FIG. 13, whole digestate (i.e., digester slurry) may be mechanically dewatered in three subsequent dewatering steps, preferably without adding polyelectrolytes or flocculant additives, resulting in (1) fibrous humid cake, (2) sludge (e.g., decanter sludge cake), and (3) a fine-particles slurry. An exemplary composition of the fibrous humid cake is about 25 wt % total solids, about 0.5 wt % total nitrogen, about 0.7 wt % total phosphorous, and about 0.3 wt % total potassium. An exemplary composition of the decanter sludge cake is about 5 wt % total solids, about 1 wt % total nitrogen, about 0.5 wt % total phosphorous, and about 0.6 wt % total potassium. Production of three different digestate products may add co-product value to the process. Any of these co-products may be dried, amended physically or chemically, and packaged. In particular, the fibrous humid cake, the decanter sludge cake, and/or the fine-particles slurry may be further dried and subsequently compressed, pelletized, blended, or a combination thereof (e.g., a blend of humid cake and sludge could be compressed and pelletized).

Referring to FIGS. 1 to 13, the biogas may be stored, sold, used, further treated (e.g., upgraded to pipeline-quality natural gas), or otherwise handled. Certain uses of the biogas include use as a fuel in gas engines or gas turbines to generate electric and thermal power; compression or liquefaction to produce renewable natural gas (RNG) in the form of compressed natural gas or liquefied natural gas; and conversion to dimethyl ether (DME) for fuel use or chemical conversion of DME to other products. The fibrous humid cake, or a derivative thereof, may be combusted for energy production, pyrolyzed for production of pyrolysis products (e.g., biochar, pyrolysis oil, etc.), used as a soil conditioner or agricultural fertilizer, used in composting such as a base material for an organic soil product, applied to a brownfield as a soil enhancement material, or employed as a landfill conditioner (cover material), for example. The fine-solids slurry, or a derivative thereof, may also be combusted for energy production, pyrolyzed for production of pyrolysis products (e.g., biochar, pyrolysis oil, etc.), used as a soil conditioner or agricultural fertilizer, used in composting such as a base material for an organic soil product, or applied to a brownfield as a soil enhancement material, for example. In various embodiments, selected nutritional compounds and/or mineral elements may be introduced during or after a drying process, to create designed soil and fertilizer products, or other co-products.

Figure 14:
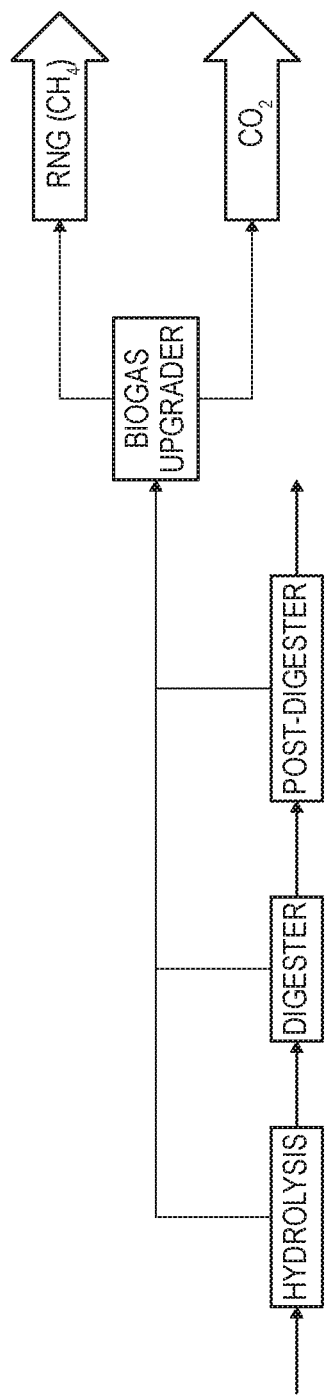
FIG. 14 depicts some process and system embodiments which collect raw biogas (containing $CH_4$ and $CO_2$, and potentially $H_2$) from a hydrolysis unit, a digester, and a post-digester, and then separating the biogas into a $CH_4$-rich stream (denoted as RNG, for renewable natural gas) and a $CO_2$-rich stream (denoted as $CO_2$).
Figure 18:
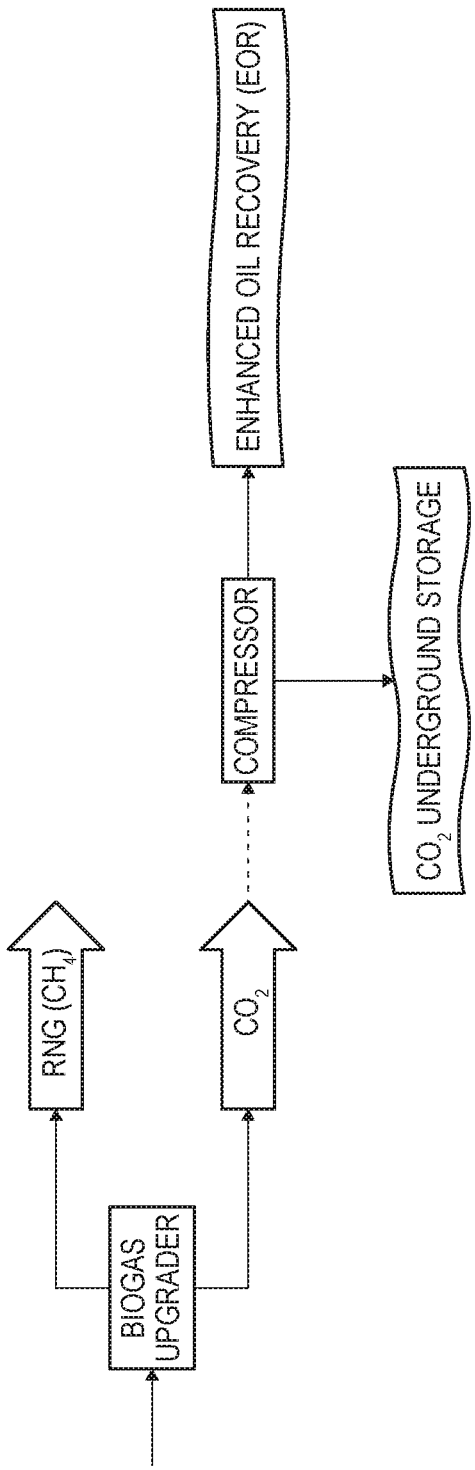
FIG. 18 depicts some process and system embodiments which inject captured $CO_2$ from a biogas upgrading system into an underground cavern or geological storage horizon, where the $CO_2$ may be stored indefinitely, thereby sequestering $CO_2$, or where the captured $CO_2$ is used for enhanced oil recovery (EOR) of fossil oil fields.
Figure 19:
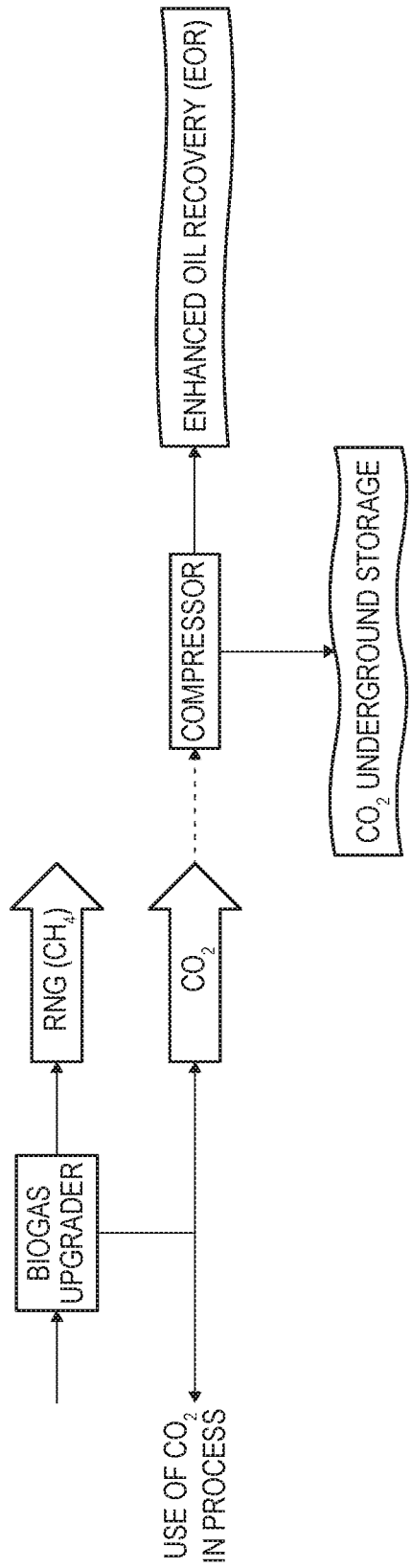
FIG. 19 depicts some process and system embodiments which inject a portion of captured $CO_2$ from a biogas upgrading system into an underground cavern or geological storage horizon, where the $CO_2$ may be stored indefinitely, thereby sequestering $CO_2$, or where the captured $CO_2$ is used for enhanced oil recovery (EOR) of fossil oil fields; and the remainder of the $CO_2$ is reused in the process.
Figure 20:
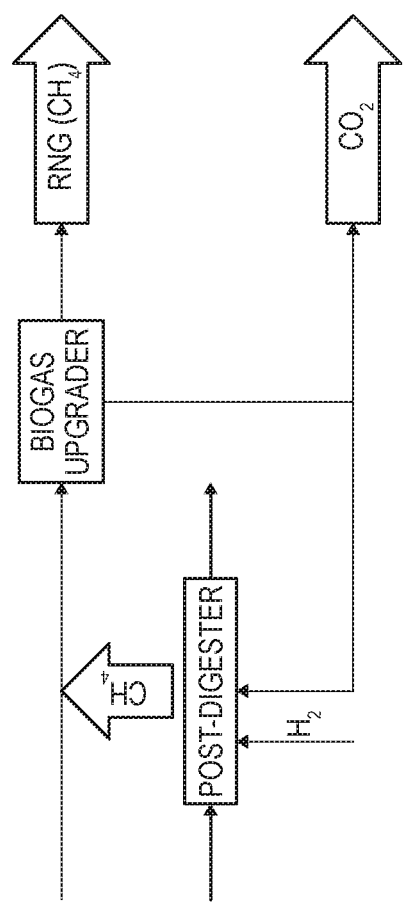
FIG. 20 depicts some process and system embodiments which separate raw biogas to $CH_4$ and $CO_2$, wherein the $CO_2$ is recycled to generate additional methane in a post-digester using hydrogenotrophic and/or acetoclastic bacteria.

Referring to FIG. 14, some process embodiments use, re-use, or sequester carbon dioxide ($CO_2$). In the process of FIG. 14, raw biogas (containing $CH_4$ and $CO_2$) is collected from a hydrolysis unit, a digester, and a post-digester. The raw biogas is fed to a biogas upgrader, which at a minimum separates the biogas into a $CH_4$-rich stream (denoted as RNG, for renewable natural gas) and a $CO_2$-rich stream (denoted as $CO_2$). Other separation or purification steps may be applied in the biogas upgrader, including dehydration and/or desulfurization. $H_2O$ and sulfur compounds (e.g., $H_2S$ or $SO_2$) removed during dehydration and desulfurization, respectively, may be separately recovered from the $CO_2$. Biogas conditions such as pressure and temperature may be adjusted. The RNG is preferably a clean methane stream that complies with pertinent local regulations for further use of RNG, including fueling, bottling, pipeline injection, or processing of the methane into other gaseous or liquid products. In FIG. 14, the $CO_2$ stream is released to the atmosphere, as is conventional for methane upgrading systems. In some embodiments (such as shown in FIGS. 18 and 19), the $CO_2$ is not emitted to the atmosphere but rather is sequestered, such as in underground storage.

Figure 15:
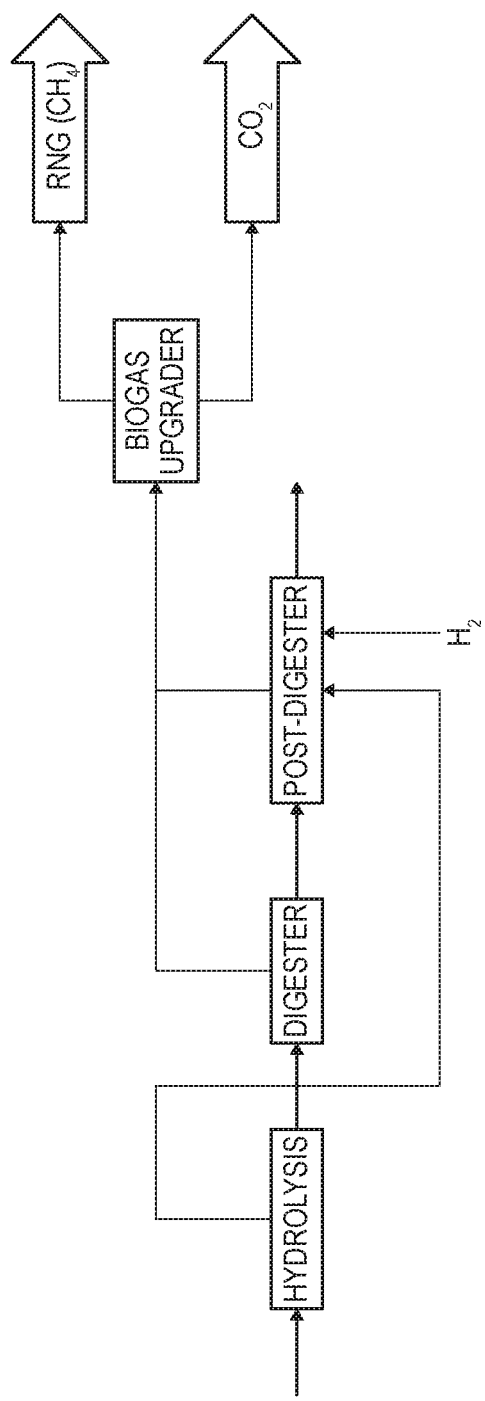
FIG. 15 depicts some process and system embodiments which employ hydrogenotrophic and/or acetoclastic bacteria to convert $H_2$ and $CO_2$ biologically into $CH_4$ in a post-digester.

Referring to FIG. 15, the process in some embodiments utilizes the capability of a certain group of anaerobic bacteria—namely, hydrogenotrophic bacteria—to convert $H_2$ and $CO_2$ biologically into $CH_4$. The conversion is well-known as one of the natural pathways within bacteria that may be active in an anaerobic digester.

In a typical anaerobic digestion process, the last step of forming $CH_4$ is carried out by two reactions processes involving distinct bacteria. In one reaction, hydrogenotrophic bacteria utilize $H_2$ and $CO_2$ to form $CH_4$, according to the simplified overall reaction $4H_2+CO_2 \rightarrow CH_4+2\ H_2O$ (hereinafter, pathway A), which is highly exothermic, $\Delta H=-131$ kJ/mol. In another reaction, acetoclastic bacteria utilize acetic acid to form $CH_4$ (hereinafter, pathway B). Typically, in an anaerobic primary digester, both reactions take place in parallel, wherein (for illustration purposes) approximately two-thirds of the methane is formed via pathway B and only one-third of the total methane is formed via pathway A. In a post-digester, on the other hand, the concentration of acetic acid is typically very low, because acetic acid is already converted in the upstream primary digester into biogas. Thus, in a post-digester, pathway A can be the predominant reaction pathway, if sufficient amounts of $H_2$ and $CO_2$ are available.

The presence and concentration of acetic acid will generally dictate which pathway is established by the bacteria, in a digester or a post-digester. When more acetic acid is present, pathway B is preferred over pathway A, because reactant concentrations are higher for pathway B (driving the reaction forward) and because acetic acid causes inhibition of hydrogenotrophic bacteria. Acetic acid itself can be a fermentation product, when acetic acid bacteria (Acetobacteraceae) are present, along with a source of oxygen (which may be unreacted oxygen from microaeration applied in hydrolysis, for example). In addition, many lignocellulosic feedstocks contain high concentrations of acetyl groups, which readily generate acetic acid during pretreatment.

The process of FIG. 15 employs a main digester to remove and convert some, most, or all acetic acid into biogas, resulting in a low (or zero) acetic acid concentration entering the post-digester. The post-digester is provided as a reaction vessel for the above-described hydrogenotrophic conversion, pathway A. In order to achieve good hydrogenotrophic yields, gases rich in $H_2$ (and potentially $CO_2$) are directed into the post-digester. The $H_2$ and $CO_2$ are converted by pathway A, in the presence of hydrogenotrophic bacteria, into $CH_4$. To achieve good conversion of $H_2$ and $CO_2$, the gas feed to the post-digester, or the volume within the post-digester, has a stoichiometric molar ratio of $H_2$ to CO from about 1 to about 10, such as from about 3 to about 6, and preferably about 4. Note that depending on the concentration of $CO_2$ present in the post-digester, $CO_2$ may or may not need to be added to the post-digester from other sources, such as $CO_2$ generated in hydrolysis (as shown in FIG. 15) from the primary digester, of from the biogas upgrading unit that separates out $CO_2$.

The source of $H_2$ for injection to the post-digester may be any available source, such as bottled hydrogen, on-site hydrogen production, or hydrogen from an adjacent site. When hydrogen is generated internally, one preferred technique is electrolysis to split water into $H_2$ and $O_2$, using electrical power that may be generated also on-site, such as via combustion of solid digestate and/or lignin, or via wind power, for example.

Gas injection into the post-digester may be accomplished by gas lances, gas diffusers or nozzles located at the bottom or the sidewalls of the post-digester, gas injectors for injecting gases into the slurry feed of the post-digester, gas injectors for injecting gases into a recirculation line of the post-digester, or a combination thereof. It is preferred to provide sufficient reaction time for the injected gases after their injection into the post-digester. In some embodiments, sufficient reaction time is provided with a post-digester diameter-to-height ratio of at least 0.3, and preferably at least 0.6, such as about 1.0.

Because the hydrogenotrophic formation of methane is exothermic, in some embodiments the post-digester requires no additional heating. In certain embodiments, excess heat in the post-digester is recovered via internal or external heat exchangers, for heating the digester or for other process heating requirements.

Generally speaking, hydrogen may be introduced to the process to react with residual carbon dioxide in any unit operation, thereby forming additional methane, via pathway A.

Figure 16:
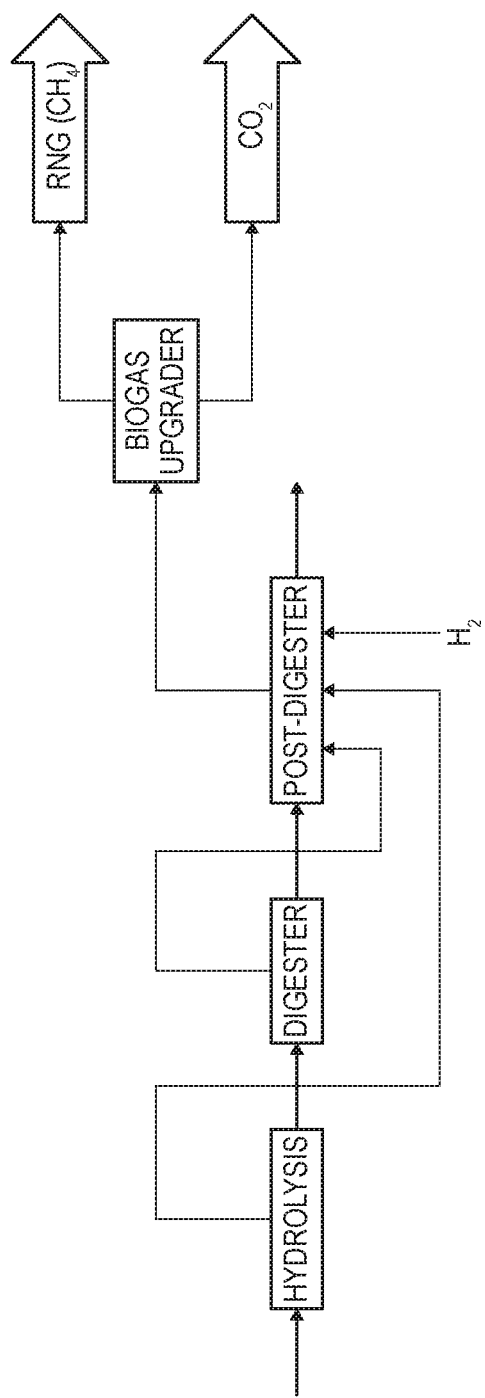
FIG. 16 depicts some process and system embodiments which employ hydrogenotrophic and/or acetoclastic bacteria to convert $H_2$ and $CO_2$ biologically into $CH_4$ in a post-digester, with the biogas generated in the digester redirected into the post-digester.

Referring to FIG. 16, the process in some embodiments utilizes the capability of hydrogenotrophic bacteria to convert $H_2$ and $CO_2$ biologically into $CH_4$. FIG. 16 is similar to FIG. 15, except that biogas generated in the digester is redirected into the post-digester, rather than being captured directly. The advantage is that the $CO_2$ produced in the digester is utilized via pathway A in the post-digester, and additional $CO_2$ may not need to be injected into the post-digester. $CH_4$ produced in the digester, and conveyed to the post-digester, is not consumed by hydrogenotrophic bacteria, which also generate additional $CH_4$. The total $CH_4$ is captured from the post-digester, for upgrading in the biogas upgrader.

Figure 17:
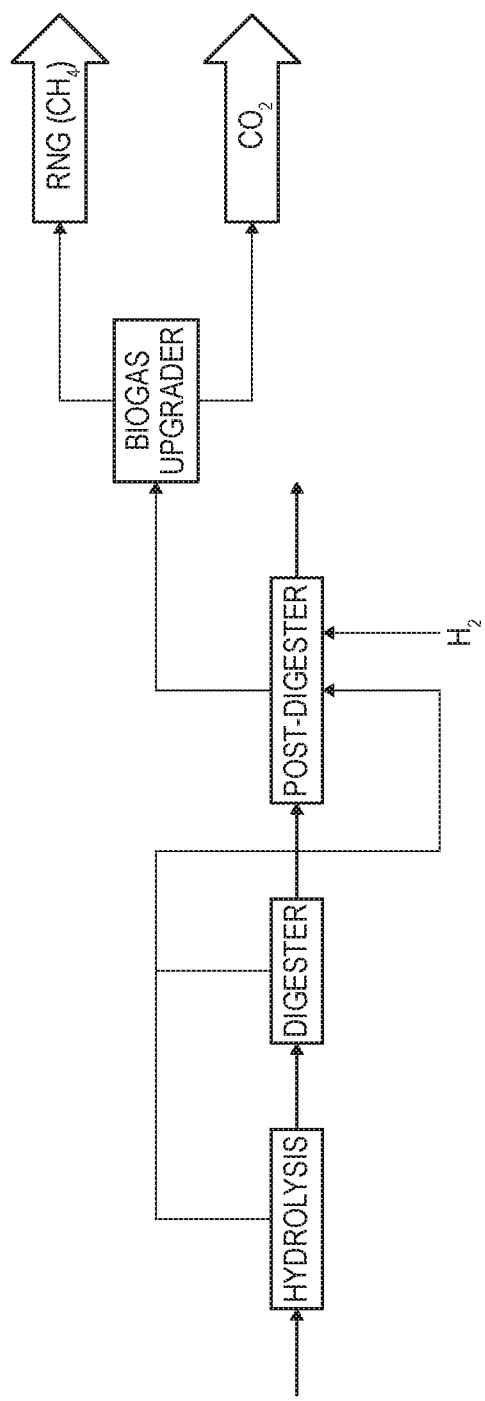
FIG. 17 depicts some process and system embodiments which employ hydrogenotrophic and/or acetoclastic bacteria to convert $H_2$ and $CO_2$ biologically into $CH_4$ in a post-digester, with the biogas generated in the digester and the hydrolysis unit combined and then redirected into the post-digester.

Referring to FIG. 17, the process in some embodiments utilizes the of capability hydrogenotrophic bacteria to convert $H_2$ and $CO_2$ biologically into $CH_4$. FIG. 17 is similar to FIG. 16, except that gases from the hydrolysis unit and the digester are first combined before injection into the post-digester.

Referring to FIG. 18, the process in some embodiments injects captured $CO_2$ from the biogas upgrading system into an underground cavern or geological storage horizon, where the $CO_2$ may be stored indefinitely, thereby sequestering $CO_2$. The $CO_2$ is preferably compressed, and potentially liquefied, before injecting underground. The underground cavern or geological storage horizon is preferably contained in an active or abandoned oil or natural gas field.

Referring to FIG. 19, the process in some embodiments injects a portion of captured $CO_2$ from the biogas upgrading system into an underground cavern or geological storage horizon, where the $CO_2$ may be stored indefinitely, thereby sequestering $CO_2$. $CO_2$ is preferably compressed, and potentially liquefied, before injecting underground. The remainder of the $CO_2$ is reused in the process, such as to assist in generation of additional methane via pathway A in the digester and/or post-digester (e.g., see FIG. 20), to act as a pretreatment chemical, to serve as a solvent, or for other process uses. Also note that the $CO_2$ may be purified and sold as a beverage additive, an input substrate for greenhouses, or other commercial products.

Generally, with respect to FIGS. 15 to 20, several commercial and environmental benefits may be achieved. Surplus (otherwise wasted) $CO_2$ is instead converted into more methane product for sale. $CO_2$ is sequestered into a fuel (methane) and/or into permanent geological storage, for example. The overall $CO_2$ footprint of a biogas plant, operating the disclosed processes, is reduced.

In this detailed description, reference has been made to multiple embodiments and to the accompanying drawings in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The recited process options and process embodiments may be utilized entirely or partially. Some embodiments may omit process steps. Some embodiments include other process steps that are not explicitly taught herein but are conventional in the chemical-engineering and biorefinery arts. In preferred embodiments, a combination of process options and process embodiments is configured to optimize overall biogas products and/or production of co-products.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. A process for converting a lignocellulosic feedstock into methane, said process comprising:
    (a) grinding or milling a lignocellulosic feedstock, to generate a size-reduced lignocellulosic material, wherein said size-reduced lignocellulosic material optionally contains water moisture but contains no free liquid;
    (b) optionally introducing a pretreatment chemical to said size-reduced lignocellulosic material;

(c) pelletizing or extruding said size-reduced lignocellulosic material, to generate a plurality of lignocellulosic pellets or extrudates;
(d) forming an intermediate slurry from at least some of said lignocellulosic pellets or extrudates;
(e) continuously or semi-continuously feeding said intermediate slurry into one or more anaerobic digesters operated at effective fermentation conditions to generate methane-containing biogas and a digester slurry; and
(f) recovering said methane-containing biogas from said one or more anaerobic digesters.

2. The process of claim 1, wherein said lignocellulosic feedstock is selected from the group consisting of grass straw, wheat straw, corn stover, grain straw, rice straw, cotton burr, sugarcane bagasse, and combinations thereof.

3. The process of claim 1, wherein said size-reduced lignocellulosic material has an average maximum particle size of about 1 inch or less.

4. The process of claim 1, wherein a waste feedstock is also fed to said one or more anaerobic digesters.

5. The process of claim 4, wherein said waste feedstock is selected from the group consisting of food waste, agricultural organic waste, industrial organic waste, livestock manure, and combinations thereof.

6. The process of claim 4, wherein the weight ratio of said lignocellulosic feedstock to said waste feedstock is selected from about 0.3 to about 3.0.

7. The process of claim 1, wherein said pretreatment chemical is selected from the group consisting of sodium hydroxide, potassium hydroxide, calcium carbonate, ammonia, acetic acid, phosphoric acid, urea, carbon dioxide, salts of any of the foregoing, and combinations thereof.

8. The process of claim 1, wherein said pretreatment chemical is present in a concentration from about 0.1 wt % to about 10 wt % based on the combined weight of said size-reduced lignocellulosic material and said pretreatment chemical, on a dry basis.

9. The process of claim 1, wherein steps (b) and (c) are performed simultaneously.

10. The process of claim 1, wherein said lignocellulosic pellets or extrudates are in the form of lignocellulosic cubes.

11. The process of claim 10, wherein said lignocellulosic cubes have an average minimum length scale selected from about 0.1 inch to about 6 inches.

12. The process of claim 10, wherein said lignocellulosic cubes have an average maximum length scale selected from about 0.5 inch to about 12 inches.

13. The process of claim 1, wherein step (c) includes pelletizing at a pelletizing temperature selected from about 25° C. to about 150° C.

14. The process of claim 1, wherein step (c) includes extruding to generate lignocellulosic extrudates.

15. The process of claim 14, wherein said extruding is at an extrusion temperature selected from about 50° C. to about 250° C.

16. The process of claim 14, wherein said lignocellulosic extrudates are formed in a double-screw extruder configured with two counter-rotating screws.

17. The process of claim 1, wherein said lignocellulosic pellets or extrudates are conveyed from a first location to a second location within said process.

18. The process of claim 1, wherein step (d) is conducted.

19. The process of claim 1, said process further comprising a hydrolysis step including (i) hydrolysis of said size-reduced lignocellulosic material and/or (ii) hydrolysis of said intermediate slurry, prior to step (e).

20. The process of claim 19, wherein said hydrolysis step includes enzymatic hydrolysis with micro-aeration of said size-reduced lignocellulosic material and/or said intermediate slurry.

21. The process of claim 19, wherein said hydrolysis step is conducted at a hydrolysis temperature selected from about 50° C. to about 70° C.

22. The process of claim 19, said process further comprising recycling said digester slurry, or a solid digestate derived therefrom, back to said hydrolysis step.

23. The process of claim 1, wherein said effective fermentation conditions include a fermentation temperature selected from about 20° C. to about 70° C.

24. The process of claim 1, wherein said effective fermentation conditions include a fermentation pH selected from about 6.5 to about 8.5.

25. The process of claim 1, wherein said effective fermentation conditions include a fermentation time selected from about 5 days to about 60 days.

26. The process of claim 1, wherein said effective fermentation conditions include presence of a thermophilic microorganism and/or a mesophilic microorganism.

27. The process of claim 1, wherein said effective fermentation conditions include presence of enzymes to enhance degradation rate of cellulose and/or hemicellulose.

28. The process of claim 1, said process further comprising a post-digestion step including addition of enzymes to enhance degradation rate of residual lignocellulosic fibers.

29. The process of claim 1, wherein said effective fermentation conditions include a total suspended solids from about 1 wt % to about 40 wt %, and wherein organic dry matter content is from about 30 wt % to about 90 wt % of said total suspended solids.

30. The process of claim 1, wherein said methane-containing biogas is purified to generate an upgraded biogas with higher methane content compared to said methane-containing biogas.

31. The process of claim 30, wherein said upgraded biogas contains at least 90 vol % methane.

32. The process of claim 1, wherein said methane-containing biogas contains carbon dioxide, and wherein said carbon dioxide is separated and recovered.

33. The process of claim 32, wherein at least some of said carbon dioxide is sequestered into a geological formation.

34. The process of claim 1, said process further comprising recovery of a nitrogen-containing compound from said digester slurry.

35. The process of claim 1, said process further comprising separating said digester slurry into a liquid digestate and a solid digestate.

36. The process of claim 35, wherein said liquid digestate is recovered as a co-product selected from the group consisting of a fuel, biochar, pyrolysis oil, soil conditioner, agricultural fertilizer, organic soil product, soil enhancement material, landfill conditioner, and combinations thereof.

37. The process of claim 35, wherein said liquid digestate is recovered as a co-product that is a fine-particles slurry containing from about 1 wt % to about 10 wt % total solids, from about 0.2 wt % to about 4 wt % nitrogen, from about 0.05 wt % to about 2 wt % phosphorous, and from about 0.1 wt % to about 2 wt % potassium.

38. The process of claim 35, wherein said liquid digestate is recycled to step (b) and/or step (c).

39. The process of claim 38, wherein said liquid digestate is utilized to directly generate steam that steam-extracts or steam-explodes said size-reduced lignocellulosic material and/or said lignocellulosic pellets or extrudates.

40. The process of claim 35, wherein said liquid digestate is recycled to step (e), and wherein said liquid digestate has a ratio of carbon to nitrogen, on an elemental weight basis, of 30 or less.

41. The process of claim 35, wherein said solid digestate is recovered as a co-product selected from the group consisting of a solid fuel, biochar, pyrolysis oil, soil conditioner, agricultural fertilizer, organic soil product, soil enhancement material, landfill conditioner, and combinations thereof.

42. The process of claim 41, wherein said solid digestate is recovered as a co-product that is a fibrous humid cake containing from about 10 wt % to about 50 wt % total solids, from about 0.1 wt % to about 2 wt % nitrogen, from about 0.1 wt % to about 3 wt % phosphorous, and from about 0.05 wt % to about 1 wt % potassium.

43. The process of claim 35, wherein said solid digestate is recycled back to said one or more anaerobic digesters.

* * * * *